(12) United States Patent
Pendurthi et al.

(10) Patent No.: US 9,808,505 B2
(45) Date of Patent: Nov. 7, 2017

(54) SUPPRESSION OF MALIGNANT MESOTHELIOMA BY OVEREXPRESSION OR STIMULATION OF ENDOTHELIAL PROTEIN C RECEPTORS (EPCR)

(71) Applicant: BOARD OF REGENTS, THE UNIVERSITY OF TEXAS SYSTEM, Austin, TX (US)

(72) Inventors: Usha R. Pendurthi, Tyler, TX (US); Vijaya M. R. Lella, Tyler, TX (US); Shivakeshava Gaddam, Tyler, TX (US); Steven Idell, Tyler, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/765,922

(22) PCT Filed: Mar. 10, 2014

(86) PCT No.: PCT/US2014/022373
§ 371 (c)(1),
(2) Date: Aug. 5, 2015

(87) PCT Pub. No.: WO2014/138727
PCT Pub. Date: Sep. 12, 2014

(65) Prior Publication Data
US 2015/0366939 A1    Dec. 24, 2015

Related U.S. Application Data

(60) Provisional application No. 61/775,251, filed on Mar. 8, 2013.

(51) Int. Cl.
| | |
|---|---|
| *A61K 38/17* | (2006.01) |
| *A61K 48/00* | (2006.01) |
| *C12N 15/113* | (2010.01) |
| *A61K 9/00* | (2006.01) |
| *A61K 31/4439* | (2006.01) |
| *A61K 31/5377* | (2006.01) |
| *A61K 38/19* | (2006.01) |
| *A61K 38/21* | (2006.01) |

(52) U.S. Cl.
CPC ............ *A61K 38/177* (2013.01); *A61K 9/007* (2013.01); *A61K 9/0019* (2013.01); *A61K 31/4439* (2013.01); *A61K 31/5377* (2013.01); *A61K 38/191* (2013.01); *A61K 38/217* (2013.01); *A61K 48/005* (2013.01); *A61K 48/0058* (2013.01); *C12N 15/113* (2013.01); *C12N 2310/14* (2013.01); *C12N 2310/531* (2013.01); *C12N 2710/10343* (2013.01); *C12N 2710/10371* (2013.01)

(58) Field of Classification Search
None
See application file for complete search history.

(56) References Cited

U.S. PATENT DOCUMENTS 7,638,122 B2 * 12/2009 Yu ................ A61K 39/0011
424/93.71
2016/0199513 A1 * 7/2016 Bancel ............... A61K 31/7088
514/44 R

FOREIGN PATENT DOCUMENTS

| WO | 2004080394 A2 | 12/2004 |
| WO | 2007115269 A2 | 10/2007 |
| WO | 2010130757 A1 | 11/2010 |

OTHER PUBLICATIONS

Keshava et al., Endothelial Cell Protein C Receptor Opposes Mesothelioma Growth Driven by Tissue Factor Cancer research Jul. 2013 vol. 73, Issue 13 pp. 3163-3973.*
Heng et al., Inhibition of Cellular Growth and Migration by Suppression of Endothelial Protein C Receptor (EPCR) in Lung Carcinoma Cells Oncology Research Featuring Preclinical and Clinical Cancer Therapeutics, vol. 20, Nos. 5-6, 2012, pp. 231-240(10) Abstract.*
Keshava et al., Endothelial Cell Protein C Receptor Promotes Apoptosis in Malignant Pleural Mesothelioma Cells Blood, (Dec. 3, 2015) vol. 126, No. 23.Meeting Info.: 57th Annual Meeting of the American-Society-of-Hematology. Orlando, FL, USA. Dec. 5-8, 2015, Abstract.*
Endothelial cell protein C receptor (EPCR)—Nucleotide—NCBI, pp. 1-3, last visited Sep. 8, 2016.*
Perurena-Aizcorbe et al., Role of EPCR in breast cancer progression and metastasis University of Navarra School of Sciences Aug. 27, 2015 pp. 1-155.*
Ngo, in the Protein Folding Problem and Tertiary Structure Prediction, Merz et al. (eds.), Birkhauser Boston: Boston, MA, pp. 433 and 492-495, 1994.*

(Continued)

*Primary Examiner* — Maria Leavitt
(74) *Attorney, Agent, or Firm* — Browdy and Neimark, PLLC

(57) ABSTRACT

The influence of TF, endothelial cell protein C receptor (EPCR) and protease activated receptor-1 (PAR1) on tumor growth of malignant pleural mesothelioma (MPM) is disclosed. MPM cells that lack or express TF, EPCR or PAR1 and a murine orthotopic model of MPM led to the discovery that intrapleural administration into nude mice of REN MPM cells expressing TF and PAR1 but lacking EPCR and PAR2 generated large pleural cavity tumors. Suppression of TF or PAR1 expression markedly reduced tumor growth. Overexpression of TF in non-aggressive MPM cells expressing EPCR and PAR1 but exhibiting minimal levels of TF failed to alter their tumorigenicity. Introduction of EPCR expression in aggressive MPM cells attenuated tumor growth whereas EPCR silencing in non-aggressive MPM cells overexpressing TF increased tumorigenicity of non-aggressive cells. Expression of EPCR by MPM cells suppresses tumor growth and treats MPM.

3 Claims, 21 Drawing Sheets

(56) References Cited

OTHER PUBLICATIONS

Rudinger (in Peptide Hormones, Parsons (ed.), University Park Press: Baltimore, MD, pp. 1-7, 1976.*
Gorecki et al., Prospects and problems of gene therapy: an update Erpert Opin. Emerging Drugs (2001) 6(2):187-178.*
Kimchi-Sarfaty C et al., A "silent" polymorphism in the MDR1 gene changes substrate specificity.Science. Jan. 26, 2007;315(5811):525-8.*
uspto.gov/web/offices/pac/writtendescription.pdf downloaded Mar. 20, 2017 pp. 1-66.*
F Hayakawa et al., "A novel STAT inhibitor, OPB-31121, has a significant antitumor effect on leukemia with STAT-addictive oncokinases", Blood Cancer Journal 3: pp. 1-9 (e166) (Nov. 2013).
Weitz, J. et al., "New Anticoagulant Drugs—7th Seventh ACCP Conference on Antithrombotic and Thrombolytic Therapy", Chest 126, pp. 265S-286S (2004).
Vachani A, Sterman DH, Albelda SM, "Cytokine gene therapy for malignant pleural mesothelioma," J Thorac Oncol, 2, pp. 265-267 (2007).
Gordon, GJ et al., "Identification of Novel Candidate Oncogenes and Tumor Suppressors in Malignant Pleural Mesothelioma Using Large-Scale Transcriptional Profiling", Am. J. Pathol. 166, pp. 1827-1840 (2005).
Gordon, GJ., et al., "Validation of Genomics-Based Prognostic Tests in Malignant Pleural", Mesothelioma et al., Clin Cancer Res 11, pp. 4406-4414 (2005).
Fukazawa T et al., "Malignant pleural mesothelioma-targeted CREBBP/EP300 inhibitory protein 1 promoter system for gene therapy and virotherapy", Cancer Res., 68, pp. 7120-7129 (2008).
Hassan R et al. "Mesothelin: A New Target for Immunotherapy", Clin Cancer Res, 10, pp. 3937-3947 (2004).
Hucl, T et al., "High Cancer-Specific Expression of Mesothelin (MSLN) is Attributable to an Upstream Enhancer Containing a Transcription Enhancer Factor—Dependent MCAT Motif,"Cancer Res, 67, pp. 9055-9065 (2007).
GenBank: EF420155.1—*Homo sapiens* mesothelin (MSLN) mRNA, 5' UTR (2007).
Bezuhly M, Cullen R, Esmon CT, Morris SF, West KA, Johnston B, et al. "Role of activated protein C and its receptor in inhibition of tumor metastasis", Blood, 113, pp. 3371-3374, (2009).
Williams L, Tucker TA, Koenig K, Allen T, Rao LV, Pendurthi U, et al. "Tissue Factor Pathway Inhibitor Attenuates the Progression of Malignant Pleural Mesothelioma in Nude Mice" Am J Respir Cell Mol Biol, (2011).
Beaulieu LM, Church FC, "Activated protein C promotes breast cancer cell migration through interactions with EPCR and PAR-1" Exp Cell Res, 313, pp. 677-687,(2007).
Gramling MW, Beaulieu LM, Church FC, "Activated protein C enhances cell motility of endothelial cells and MDA-MB-231 breast cancer cells by intracellular signal transduction", Exp Cell Res, 316 pp. 314-328 (2010).
Van Sluis GL, Niers TM, Esmon CT, Tigchelaar W, Richel DJ, Buller HR, et al., "Endogenous activated protein C limits cancer cell extravasation through sphingosine-1-phosphate receptor 1-mediated vascular endothelial barrier enhancement," Blood, 114, pp. 1968-1973 (2009).
Anton I, Molina E, Luis-Ravelo D, Zandueta C, Valencia K, Ormazabal C, et al, "Receptor of Activated Protein C Promotes Metastasis and Correlates with Clinical Outcome in Lung Adenocarcinoma", Am J Respir Crit Care Med, (2012).
Tsuneyoshi N, Fukudome K, Horiguchi S, Ye X, Matsuzaki M, Toi M, et al, "Expression and anticoagulant function of the endothelial cell protein C receptor (EPCR) in cancer cell lines", Thromb Haemost, 85, pp. 356-361 (2001).
Scheffer GL, Flens MJ, Hageman S, Izquierdo MA, Shoemaker RH, Scheper RJ, "Expression of the vascular endothelial cell protein C receptor in epithelial tumour cells," Eur J Cancer, 38, pp. 1535-1542, (2002).
Van der Most RG, Robinson BW, Nelson DJ, "Gene therapy for malignant mesothelioma: beyond the infant years" Cancer Gene Ther, 13, pp. 897-904, (2006).

* cited by examiner

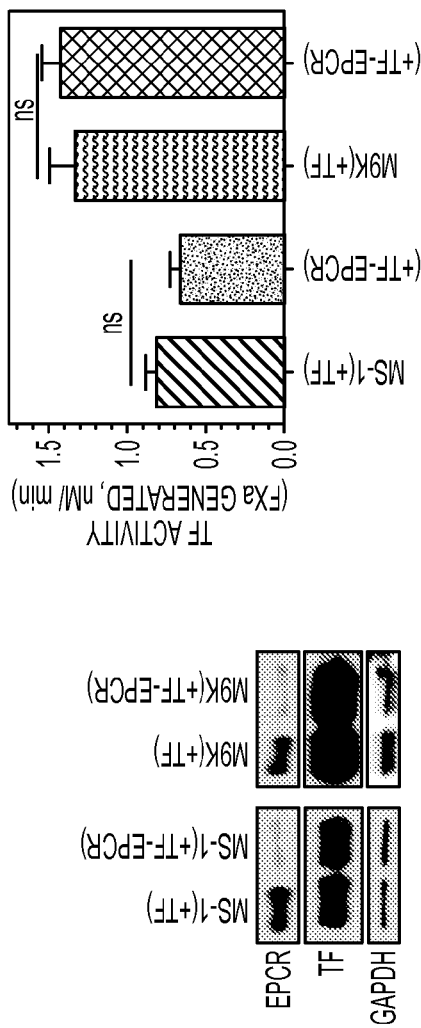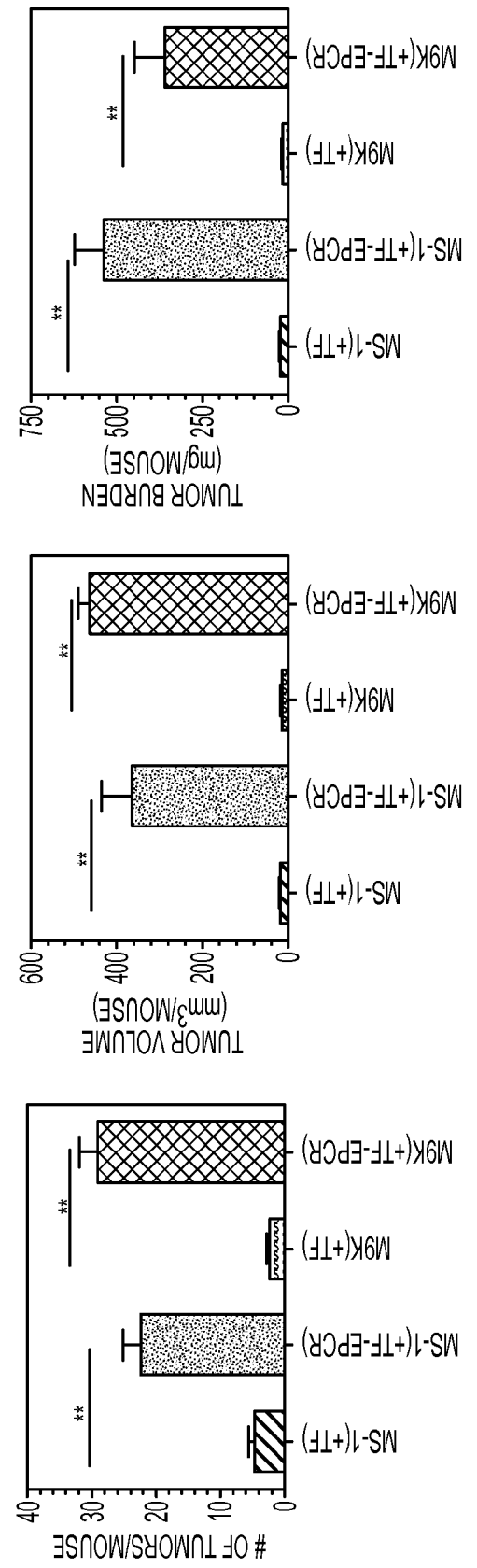
FIG. 7A FIG. 7B FIG. 7C FIG. 7D FIG. 7E

SUPPRESSION OF MALIGNANT MESOTHELIOMA BY OVEREXPRESSION OR STIMULATION OF ENDOTHELIAL PROTEIN C RECEPTORS (EPCR)

BACKGROUND OF THE INVENTION

Field of the Invention

The invention in the field of biochemistry, molecular biology and medicine relates to the suppression of growth and metastasis of malignant pulmonary mesothelioma (MPM) cells and the treatment of MPM using nucleic acid vectors, or endothelial protein C receptor (EPCR) agonists in the form of polypeptides, peptides or small organic molecules.

Description of the Background Art

It has been well recognized for many decades that tumors dramatically increase the risk for hemostatic abnormalities such as disseminated intravascular coagulation, pulmonary and venous thromboembolism (1-3). Prior studies have also established that hemostatic factors play a major role in cancer biology, particularly in tumor dissemination and metastasis (4-6). Tumor cell-associated tissue factor (TF) is known to contribute to tumor growth and progression either directly by TF-FVIIa or TF cytoplasmic tail-mediated cell signaling (7-9) or indirectly through generation of thrombin that leads to activation of platelets, fibrin deposition and activation of protease-activated receptor-1 ("PAR1")-mediated cell signaling (10-13). Consistent with the importance of thrombin in tumor biology, endothelial cell protein C receptor (EPCR) and thrombomodulin (TM), two transmembrane glycoproteins present on endothelial cells that impair thrombin generation were found to diminish tumor metastasis (14-16).

EPCR belongs to the Class 1 MHC family of receptors. TF belongs to Class 2 cytokine receptor family. Both have short cytoplasmic tails implicated in cell signaling. EPCR is constitutively expressed in endothelium, acts as the receptor for anti-coagulant protein C cofactor to enhance cleavage of clotting factors Factor V (FV) and Factor VIII (FVIII). EPCR was subsequently found to be expressed on many cell types. TF is constitutively expressed on perivascular cells and cancer cells. TF is a cofactor for FVIIa that initiates the clotting cascade. In response to inflammatory stimuli, TF is induced in many cell types. The role(s) of EPCR and TF on tumor growth in general, and of malignant pleural mesothelioma (MPM) in particular, are largely unknown.

Mesothelioma is a rare but serious cancer of the membranous tissue that covers majority of internal organs. Most often it occurs in the pleural membranes covering lungs, heart and diaphragm and is called the pleural mesothelioma. It is also found in the peritoneum and testicular membrane. Mesothelioma is prevalent in workers and handlers of asbestos. Most mesothelioma patients die within 4-18 months after diagnosis. Five year survival is only 5-10% and so far there is no cure.

Recent studies showed promotion of tumor growth by TF independent of its role in coagulation (17-20). Selective inhibition of TF-FVIIa signaling using a specific monoclonal antibody ("mAb")—that blocks TF signaling but not TF-mediated coagulation was shown to reduce breast tumor growth (17). Blockade of protease activated receptor-2 ("PAR2") cleavage but not PAR1 cleavage by specific antibodies attenuated tumor growth. Consistent with the hypothesis that PAR2-mediated signaling contributes to tumor growth in breast cancer, mice lacking PAR2 but not PAR1, exhibited reduced tumor growth in a model of spontaneous mammary tumors (21). However, it is presently unknown whether TF-FVIIa-PAR2 signaling is responsible for TF-driven tumor growth in other types of cancers. The present inventors' recent studies on progression of MPM in nude mice showed that MPM cells that express TF generated large tumors within the pleural cavity and inhibition of tumor cell TF by overexpression of TFPI by tumor cells blocked tumor growth and invasion (22). It is presently unknown whether TF-FVIIa-PAR2-mediated cell signaling contributes to growth of MPM as was observed in breast cancer (17, 21).

The present inventors' laboratory and others have recently established that FVIIa, the clotting factor that initiates the activation of the coagulation cascade upon binding to TF, also binds to EPCR (23-25). FVIIa binding to EPCR on the endothelium or in cells expressing TF induced cell signaling by activating PAR1 either directly (26) or by enhancing TF-FVIIa-FXa cleavage of PAR1 (27). Studies in cell model systems implicated EPCR in tumor metastasis. PAR1 signaling mediated by interaction between EPCR and activated protein C ("APC") was shown to promote cancer cell migration, invasion and angiogenesis (28, 29). In vivo studies gave conflicting results as EPCR-APC signaling decreased lung metastasis in a melanoma model system by preventing tumor cell migration through enhancement of endothelial barrier function (15, 30) whereas EPCR overexpression increased metastasis in lung adenocarcinoma by promoting tumor cell survival (31). Prior to the present invention, there was no information on whether EPCR directly influences tumor growth.

TF has been found recently to contribute actively to tumor growth through a nonhemostatic, TF-dependent signaling mechanism in melanoma (19) and breast cancer (17, 21). TF supported tumor growth in breast cancer via TF-FVIIa-PAR2-mediated cell signaling, independent of PAR1 (17, 21). However, it was unclear whether such a mechanism is also responsible for tumor growth in other types of cancers. TF, in addition to facilitating TF-FVIIa binary complex-mediated activation of PAR2, can also support TF-FVIIa-FXa ternary complex activation of PAR1 (36). Moreover, studies from the inventors' laboratory and others showed that TF-FVIIa binary complex can also activate PAR1 (37).

The present inventors know of no prior reports concerning the influence of EPCR on tumor growth, though a number of studies reported that EPCR-APC signaling exerts anti-apoptotic effects on a variety of cell types (45-50). The APC/EPCR axis conferred a significant advantage in cell survival to lung adenocarcinoma cells, and this was responsible for robust prometastatic activity (31). Based upon such observations, one might have concluded that EPCR, just as TF, promotes tumor growth. However, as disclosed herein, EPCR, in fact, suppresses, tumor growth. This unexpected and novel finding runs contrary to the known functions of EPCR.

SUMMARY OF THE INVENTION

Malignant pleural mesothelioma (MPM) cells that express TF and PAR1 but not PAR2 generate large tumors in the thoracic cavity. Suppression of either TF or PAR1 reduces tumor growth in this model. However, overexpression of TF in less aggressive MPM cells that lack TF but express PAR1 failed to induce an aggressive phenotype. No EPCR expression was found in aggressive MPM cells whereas abundant EPCR expression was found in non-aggressive MPM cells. Introduction of EPCR expression to aggressive MPM cells by EPCR knock-in completely attenuated their tumorigenicity whereas the knock-down of EPCR expression in non-aggressive MPM cells that expressed TF markedly increased the tumorigenicity. This is the first discovery that EPCR acts as a tumor suppressor in MPM.

Administration of an expression vector that upregulates EPCR and treatment with agonists acting at EPCR such as Activated Protein C or agonist peptide fragments or peptide mimics thereof suppress growth and/or metastasis of MPM cells in a mammalian subject, preferably a human. Such agents are useful in the treatment of MPM.

According to the present invention, EPCR functions as a crucial negative regulator of cancer progression in MPM as it was effectively in blocking TF-driven growth of MPM tumors. The transduction of EPCR expression in aggressive MPM cells lacking EPCR promoted tumor cell apoptosis and suppressed tumor growth.

Conversely, silencing of EPCR in non-aggressive MPM cells, which constitutively express EPCR, transformed them to become highly tumorigenic by suppressing tumor cell apoptosis and promoting cell proliferation, generating aggressively growing tumors.

(1) Intrapleural administration REN MPM (REN) cells into the thoracic cavity of nude mice generated very large invasive tumors in the thoracic cavity, whereas administration of MS-1 and M9K MPM cells into nude mice produced no or very few small tumors.
(2) Tissue factor (TF) expression was markedly higher in REN cells compared to MS-1 and M9K cells. REN cells express very little EPCR, whereas both MS-1 and M9K cells express EPCR abundantly, at levels found in endothelial cells. All three MPM cell types express PAR1 and PAR2.
(3) Knock-down of TF expression in aggressive REN cells reduced tumorigenicity whereas overexpression of TF in non-aggressive MS-1 and M9K cells (similar to a level found in REN cells) failed to increase the tumorigenicity, indicating that, while TF plays a critical role in tumor growth in MPM, TF expression alone is insufficient to promote the tumor growth potential.
(4) TF-driven tumor growth of MPM depends upon PAR1-mediated signaling, shown by the knock-down of PAR1 in REN cells markedly reducing their tumorigenicity.
(5) Conferring EPCR expression on REN cells markedly reduced the number of tumors they formed, and the few tumors that were formed remained very small and non-adherent.
(6) Knock-down of EPCR expression in TF-overexpressing MS-1 and M9K cells dramatically increased the tumorigenicity of these non-aggressive MPM cells.
(7) Analysis of tumor tissue sections showed a dramatic decrease in the percentage of Ki67+ cells in tumors derived from EPCR+ cells compared to tumors from EPCR− cells. TUNEL staining (for apoptosis) showed a higher percentage of TUNEL+ cells in tumors arising from EPCR+ cells, indicating a role of EPCR in apoptosis in MPM.
(8) Conferring EPCR expression on MPM cells that lack EPCR made them highly susceptible to cell death in response to treatment with tumor necrosis factor-α (TNFα) and interferon- (IFNγ) (see FIG. 14)

Specifically, the present invention is directed to a method of treating malignant pleural mesothelioma (MPM) in a subject, comprising administering to a subject suffering from MPM, preferably intrapleurally, a nucleic acid expression vector that comprises:

(i) a nucleic acid coding sequence encoding Endothelial Protein C Receptor (EPCR),
(ii) an operably linked promoter active in MPM cells and drives expression of the EPCR-coding sequence selectively in MPM cells, and
(iii) optionally, operably linked to the coding sequence, an enhancer and/or other expression control element for expression of the EPCR-coding sequence in the MPM cells, under conditions where the MPM cells are transduced by the vector and express EPCR, wherein the expression results in killing or inhibition of growth of the MPM cells, thereby treating the MPM in the subject.

In a preferred embodiment, the nucleic acid coding sequence is
(a) SEQ ID NO:1, or
(b) a homologue or variant of SEQ ID NO:1 with at least 70% sequence identity, that encodes a polypeptide having at least 50% of the biological activity of a native EPCR polypeptide.

In another embodiment, the nucleic acid encodes a polypeptide, the amino acid sequence of which comprises:
(a) SEQ ID NO:2, or
(b) a conservative substitution variant, a fragment or an addition variant thereof that has at least 70% sequence identity with SEQ ID NO:2 and at least about 50% of the biological activity of a polypeptide with the sequence SEQ ID NO:2 in an in vitro or in vivo assay.

In the foregoing method, the promoter is preferably
(a) CREBBP/EP300 inhibitory protein-1 gene promoter; or
(b) mesothelin gene promoter further linked to a mesothelin gene enhancer element.

Also provided is a method of sensitizing MPM cells to killing by IFNγ, TNFα or a combination thereof, comprising transducing MPM cells to express EPCR, by exposing them to a nucleic acid expression vector that comprises:
(i) a nucleic acid molecule that encodes EPCR, operably linked to
(ii) a promoter that drives expression of the EPCR-coding sequence in MPM cells, and
(iii) optionally, linked to an enhancers and/or other expression control element for expression of the EPCR coding sequence in the MPM cells wherein cells so transduced have increased sensitivity to killing by IFNγ, TNFα or the combination. In a preferred embodiment of the method, the exposing is in vivo, preferably by intrapleural administration of the vector.

The invention includes a method of killing MPM cells sensitized to killing by IFNγ, TNFα, or a combination thereof, comprising,
(a) sensitizing the MPM cells as above, preferably in vivo, and
(b) exposing the sensitized cells to an effective amount of IFNγ, TNFα, or a combination thereof, thereby killing the cells.

A method of treating MPM in a subject comprises:
(a) sensitizing MPM cells in the subject as above; and
(b) administering to the subject an amount of IFNγ effective to kill the sensitized cells.

thereby treating the MPM in the subject. The above method may further comprise, in step (b) administering an amount of TNFα effective to kill the sensitized cells.

The invention is also directed to a method of suppressing MPM growth or progression in a subject, comprising administering to a subject suffering from MPM an effective amount of a pharmaceutical composition comprising:

(a) a downstream product generated by the EPCR pathway or a mimic or agonist thereof, and
(b) a pharmaceutically acceptable vehicle or excipient A preferred product in this method is a thrombin inhibitor, a Factor Xa inhibitor, or a STAT3 inhibitor.

Also provided herein is a use of a nucleic acid expression vector for treating MPM) in a subject, which vector comprises:
  (i) a nucleic acid coding sequence encoding EPCR,
  (ii) an operably linked promoter active in MPM cells and drives expression of the EPCR-coding sequence selectively in MPM cells, and
  (iii) optionally, operably linked to the coding sequence, an enhancer and/or other expression control element for expression of the EPCR coding sequence in the MPM cells wherein the MPM cells are transduced by the vector to express EPCR, and wherein the expression results in killing or inhibition of growth of the MPM cells. Preferably the vector is administered intrapleurally.

The invention is also directed to use of the above nucleic acid expression vector for the manufacture of a medicament for treatment of MPM in a subject In the above use, the nucleic acid coding sequence is preferably SEQ ID NO:1, or a homologue or variant of SEQ ID NO:1 with at least 70% sequence identity that encodes a polypeptide having at least 50% of the biological activity of a native EPCR polypeptide. In another embodiment of the above use, the nucleic acid preferably encodes a polypeptide, the amino acid sequence of which comprises:
  (a) SEQ ID NO:2, or
  (b) a conservative substitution variant, a fragment or an addition variant that has at least 70% sequence identity with SEQ ID NO:2 and at least 50% of the biological activity of an EPCR polypeptide with the sequence SEQ ID NO:2 in an in vitro or in vivo assay.

In the above use the promoter is preferably the CREBBP/EP300 inhibitory protein-1 gene or the mesothelin gene promoter linked to a mesothelin gene enhancer element. The use may further include administration of interferon γ.

Also provided is use of a downstream product of the EPCR pathway or a mimic or agonist thereof, preferably for oral administration, for suppressing MPM growth or progression in a subject and thereby treating MPM. The invention is also directed to use of the above nucleic acid expression vector for the manufacture of a medicament for treatment of MPM in a subject. The product is preferably a thrombin inhibitor, a Factor Xa inhibitor or a STAT3 inhibitor.

BRIEF DESCRIPTION OF THE DRAWINGS

FIG. 1A-1E. Varied expression of TF, EPCR, PAR1 and PAR2 in human REN, MS-1 and M9K MPM cells. FIG. 1A: TF immunoblot; FIG. 1B: Cell surface TF activity levels as measured in factor X activation assay (between group statistical significance were determined by Kruskal-Wallis test and Dunn's post test was used to evaluate the significance of differences between REN and MS-1 or M9K; ***P<0.001); FIG. 1C: EPCR immunoblot; FIG. 1D: Immunoblots for PAR1 and PAR2. Cell extract of MDA231 was a positive control for PAR1 and PAR2 expressing tumor cells; FIG. 1E: Intracellular $Ca^{2+}$ release in REN MPM cells in response to control vehicle, PAR1 agonist peptide (50 μM) or PAR2 agonist peptide (50 μM). Arrow indicates the time the control vehicle or PAR peptide agonist was added to the cells. Fl. on Y-axis indicates mean fluorescence.

FIG. 2A: Nude mice injected with MS-1, M9K or REN MPM cells ($10^6$ cells/mouse) were killed 4 weeks later and tumors generated in the thoracic cavity were measured, enumerated and weighed (n=10 to 13 mice/group, combined from two independent experiments). Statistical significance of differences between the groups were determined by the Kruskal-Wallis test; *P<0.0001. Dunn's post test was used to calculate statistical significance of differences between REN and MS-1 or M9K; *P<0.001. FIG. 2B: A representative chest cavity photograph showing tumors generated by MS-1, M9K or REN MPM cells. Arrows indicate large tumors. H, heart; L, lung. (C) H&E staining of REN tumor showing the invasion of tumor cells into diaphragm. D, diaphragm; T, tumor cells. FIG. 2D: REN tumor invading through lung tissue. T, tumor; L, lung. Image on right shows a corresponding to region shown in the white box. Tissue section was stained for collagen.

FIG. 3F: Tumors sections were processed for histology by H&E staining or immunostaining with control IgG or anti-human TF IgG.

FIG. 4F: representative images showing differences in tumor growth between mice injected with REN-p or REN-P1KD cells. Arrows indicate tumors. H, heart; L, lung.

Mice injected with naïve REN, MS-1 or M9K MPM cells, and MS-1 and M9K cells stably expressing TF were killed at the end of 30 days and tumor number (FIG. 5C), volume (FIG. 5D) and burden (FIG. 5E) were measured. Results shown in FIGS. 5C, D and E are from two independent experiments performed with two independent TF-overexpressing transfectants, which gave very similar results; n=11-14 mice/group). Statistical significance of differences between the groups was determined by Kruskal-Wallis test (***P<0.001) with Dunn's post-hoc test to compare statistical significance of differences between the two groups (ns, not significant). The tumorigenicity of MS-1 and M9K cells, controls or TF overexpressing cells, was significantly lower than that of REN MPM cells (P<0.001). FIG. 5F: Sections of tumors arising in nude mice injected with MS-1 or MS-1(+TF) cells were stained with H&E or immunostained with control IgG or anti-human TF IgG. T denotes tumor.

FIG. 6F: A representative photograph showing differences in tumor growth between mice injected with REN-Z or REN (+EPCR) cells. Arrows indicate tumors. H, heart; L, lung.

FIG. 7A-7G. Suppression of EPCR expression increases tumorigenicity of non-aggressive MPM cells expressing TF. EPCR expression in MS-1(+TF) and M9K(+TF) cells was stably knocked-down by puromycin resistant EPCR-specific shRNA plasmid. The stable transfectants were analyzed for EPCR and TF expression by western blot analysis (FIG. 7A) or cell surface TF activity in factor X activation assay (FIG. 7B). Statistical significance of differences between groups was determined by Mann-Whitney test; ns, non-significant. MS-1(+TF), MS-1(+TF-EPCR), M9K(+TF), or M9K(+TF-EPCR) MPM cells were injected intrathoracically into nude mice ($10^6$ cells/mouse). After 30 days, mice were sacrificed, and tumor number (FIG. 7C), volume (FIG. 7D) and burden (FIG. 7E) were calculated as in Example I. Statistical significance of differences between the groups was determined by Mann-Whitney test; ns, non-significant; **P<0.01. (n=5 to 6 mice/group). FIG. 7F: A representative photograph of thoracic cavities that depict marked differences in tumor growth and invasiveness in mice injected with MS-1(+TF) or MS-1(+TF-EPCR) cells. Arrows indicate tumors. H, heart; L, lung; D, diaphragm. FIG. 7G: Tumor invasion. Tumor developing in a mouse injected with M9K (+TF-EPCR) was sectioned and stained for collagen or elastin. T, tumor; L, Lung; A, airway; B, blood vessel (4×).

DESCRIPTION OF THE PREFERRED EMBODIMENTS

Figure 1E:
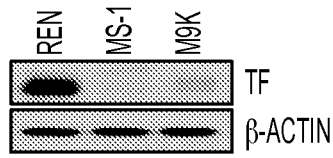
Figure 1E:
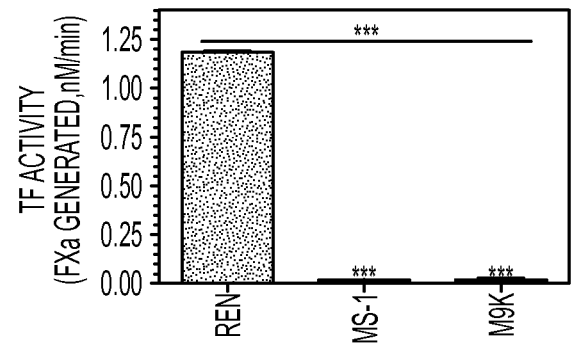
Figure 1E:
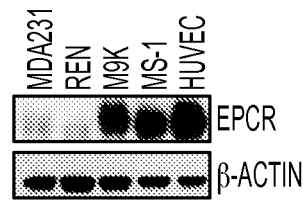
Figure 1E:
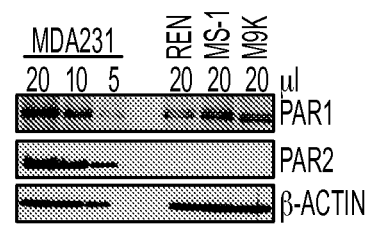
Figure 1E:
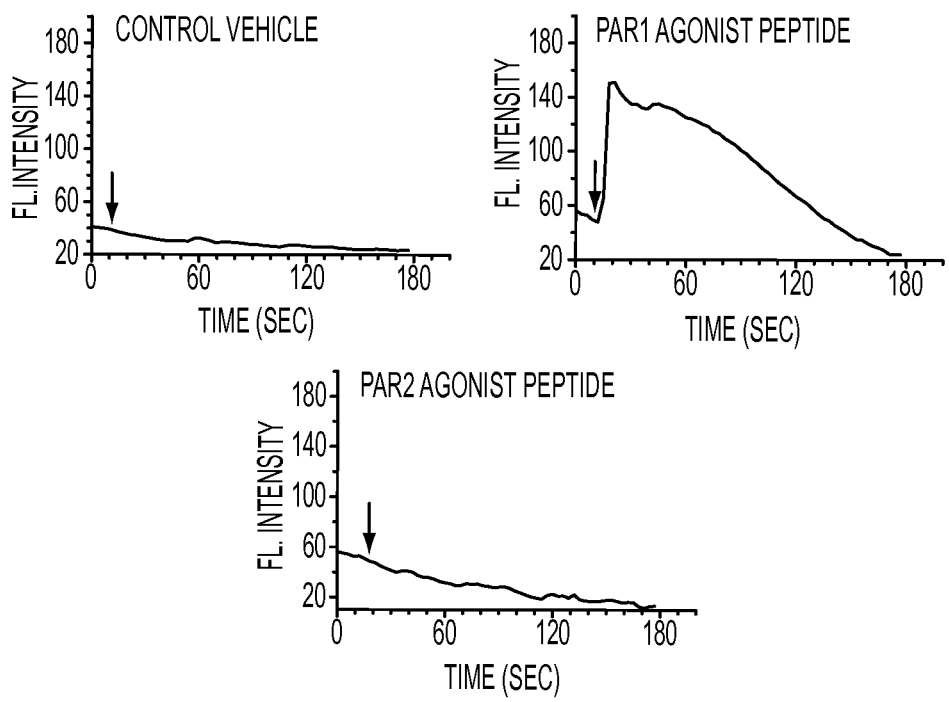

The present invention is a result of the discovery that EPCR on tumor cells acts as a potent tumor growth suppressor. The increased expression of TF in tumor cells is associated with various aspects of tumor progression, including tumor growth, angiogenesis, invasion and metastasis (7-9). Tumor cell TF-induced activation of the coagulation pathway is believed to be primarily responsible for tumor cell dissemination and metastasis as down-stream coagulation activation results in thrombin-, platelet- and fibrin-dependent pathways (6, 11, 12). In contrast, a direct tumor cell TF-mediated cell signaling was responsible for tumor growth (17). Although regulators of coagulation, such as EPCR and TM, were also shown to influence metastatic potential (15, 16, 30), their role in tumor growth was unexplored.

The present inventors used MPM cells that express or lack TF, EPCR, PAR1 and PAR2, and a novel orthotopic murine model of MPM to investigate the influence of TF and EPCR, and the requirement of TF-PAR2 signaling in MPM tumor growth. The results provided herein demonstrate that TF promotes MPM tumor growth as observed with other cancers but TF-driven tumor growth in MPM does not require PAR2 but rather is dependent on PAR1. The present results reveal that TF expression in tumor cells in itself does not fully control tumor growth as overexpression of TF in non-aggressive MPM cells expressing PAR1 failed to promote tumor growth.

The present discovery that REN MPM cells that express TF and PAR1 but not PAR2 generate large primary tumors compared to MS-1 and M9K MPM cells that express PAR1 but lack TF, and TF knock-down suppresses tumor growth of REN MPM indicate that TF drives tumor growth in MPM by a mechanism independent of PAR2. The results support the inventors' conception that TF promotes tumor growth in different cancers by different mechanisms.

Similar to TF knock-down, PAR1 knock-down also markedly suppressed REN MPM tumor growth. The extent tumor growth suppression in PAR1 knock-down appeared to be very similar to that observed with TF knock-down cells, which is consistent with the inventors' conception that TF supports MPM tumor growth via a PAR1-dependent mechanism. Direct TF-PAR1-mediated signaling or thrombin-induced PAR-1 mediated signaling may be responsible for this tumor growth. Although overall reduction in tumor growth as measured in tumor volume and burden is essentially the same in both TF- and PAR1 knock-downs, mice injected with PAR1 knock-down cells developed fewer tumors in total (average 10 tumors/mouse, including tumors <2 mm size) compared to mice injected with TF knock-down cells (average 21 tumors/mouse). Thus TF-mediated PAR1 signaling may drive primarily the tumor growth, whereas thrombin-mediated PAR1 signaling may contribute to tumor cell adhesion and initial seeding of tumor cells.

To assess whether TF promotes tumor growth in MPM through elaboration of proangiogenic factors by direct signaling (as observed in breast cancer cells (38, 39)), studies were conducted here to examine whether exposure of REN MPM cells to FVIIa increased production of proangiogenic factors in these cells. The inventors found robust or reproducible elaboration of proangiogenic factors, including IL-8, CCN1 and CCN2, in REN MPM cells in response to FVIIa. Thus, it seems unlikely that TF-FVIIa-PAR1-mediated cell signaling promotes MPM tumor growth through elaboration of proangiogenic factors as previously speculated for promotion of tumor growth in breast cancer (21). Notably, addition of FVIIa to naïve REN MPM cells increased the rate of cell proliferation by about 70%, whereas TF knock-down abrogated this FVIIa-induced increase in cell proliferation. These results indicate that TF-mediated direct signaling contributes to MPM tumor growth.

Earlier studies showed that TF expression levels determine the metastatic potential of tumor cells. Melanoma cells constitutively expressing high levels of TF were highly metastatic, whereas melanoma cells that lack TF failed to metastasize (40). Transfection of TF into non-metastatic melanoma cells positively transformed their metastatic potential (40). Similarly, transfection of CHO cells with TF enhanced tumor cell metastasis (41). A number of clinical studies found correlation between TF expression and invasiveness or clinical stage of cancer (9). Based on these observations, the present inventors predicted that transfection of non-aggressive MS-1 or M9K MPM cells with TF would increase their tumor growth potential.

Therefore, it was surprising to find that TF transfected into these cells and expressed to similar levels as was TF found in REN MPM cells failed to increase their tumor growth potential.

As noted above, while REN MPM cells lack TFPI, both MS-1 and M9K MPM cells express abundant TFPI (22). It is unlikely that suppression of TF activity by TFPI on tumor cells is the reason for the failure of MS-1 or M9K cells expressing TF to generate large tumors since TF expression levels on the transfected cells far exceed TFPI levels as selected stable transfectants were selected based on TF functional activity levels. TF functional activity in MS-1 or M9K MPM cells stably transfected with TF was similar to that of REN MPM cells. Moreover, similar TF antigen and activity levels were found in tumors excised from mice injected with (a) MS-1 or M9K cells expressing TF or (b) REN MPM cells. Overall, although TF plays a crucial role in tumor growth in MPM, TF expression alone could not establish the tumor growth potential.

An additional difference between aggressive REN MPM cells and non-aggressive MS-1/M9K MPM cells is the expression of EPCR. Both MS-1 and M9K cells express EPCR levels similar to that found in endothelial cells whereas REN cells express no or very little EPCR. This raised the possibility that EPCR acts as a tumor growth suppressor.

Unlike numerous published studies showing correlation of TF expression levels with tumor burden/metastasis and cancer survival, information on EPCR expression levels in cancer had been very limited prior to the making of the present invention. Although EPCR expressed was demonstrated in some cancer tissues (42-44), these studies were not performed systematically as they were not related to tumor grade. Expression of EPCR in tumor cells appears to be a rare event (44) and more EPCR$^+$ tumors could be found in stage pT1 than in pT2 (44).

Based upon prior (31; 41-50), one would have been led to conclude that EPCR, just as TF, promotes tumor growth.

The present invention shows that EPCR, in fact, suppresses tumor growth. This finding was novel and unexpected in light of the expectation based on prior reports (31; 41-50) that EPCR, just as TF, promotes tumor growth. This runs contrary to the known functions of EPCR. According to the present invention, tumor growth suppressive activity of EPCR requires the specific pleural microenvironment or is specific to MPM cell types.

EPCR nucleic acid and polypeptides and their respective sequences are described below.

According to one embodiment, the protective effect of EPCR on MPM tumor growth discovered here is mediated by its anticoagulant function (enhanced generation of activated protein C) or cell signaling function. EPCR, in addition to supporting cell signaling mediated by activated protein C (APC), is known to change the specificity of thrombin-PAR1-mediated cell signaling (51, 52) and promote TF-FVIIa-FXa ternary complex signaling of PAR1 and PAR2 (27). The present inventors do not believe that EPCR suppresses MPM tumor growth through its interaction with TF-FVIIa-FXa ternary signaling complex since this would be expected to promote, rather than suppress, tumor growth. due to upregulation of TF-mediated signaling in tumor cells, which in general leads to activation of pro-angiogenic and pro-tumor growth pathways (7-9). Similar to TF, PAR1 signaling is also believed to contribute to cancer progression (13). PAR1 may be involved in mediating EPCR's protective effect in suppressing tumorigenicity of MPM as EPCR was shown to switch specificity of PAR1 signaling from damaging to protective signaling (51, 52).

The molecular mechanisms by which EPCR suppresses tumor growth is not fully elucidated and the inventors do not wish to be bound by any particular mechanism. EPCR is known to primarily activate cytoprotective signaling pathways, and thus EPCR is not likely to suppress MPM tumor growth by inhibiting cell proliferation, at least directly.

The present inventors have found no significant differences in cell proliferation between MPM cells lacking EPCR expression and MPM cells expressing EPCR in the absence or presence of FVIIa, APC, thrombin or their combination under similar culture conditions.

A number of studies have shown that EPCR-mediated signaling pathway inhibits NF-κB-mediated proinflammatory pathways in monocytes and endothelial cells (46, 50, 52, 53). It is well-accepted that tumor-associated inflammatory responses play a critical role in enhancing tumorigenesis and cancer progression (54-56). In one embodiment herein, EPCR's protective effect against tumor growth occurs through its anti-inflammatory effect in a tumor microenvironment.

The present invention provides a novel therapeutic strategy for treating cancer patients, particularly MPM patients.

In one embodiment, to the extent that EPCR suppresses MPM tumor growth through enhancement of activated protein C (APC) generation, administration of exogenous APC is used to restrict the progression of this tumor, In another embodiment, to the extent that EPCR-mediated cell signaling in tumor cells is responsible for curtailing tumorigenicity, the present invention provides a method of treating MPM by transduction of EPCR into tumor cells in a "gene therapy" approach.

MPM, for which there is a shortage of effective conventional therapies. is a target for the gene therapy approaches of the present invention. This method exploits the accessibility of the tumors in the pleural space for delivery of therapeutics, and benefits from previous experience with gene therapy trials in MPM patients (57, 58).

The preferred animal subject of the present invention is a mammal. The invention is particularly useful in the treatment of human subjects. However, the present invention may also be used in veterinary medicine.

Treatment of MPM by Upregulation of EPCR-Dependent Anticoagulant or Signaling Pathways As an alternative to DNA therapy by transducing MPM cells with EPCR-encoding nucleic acid and thereby expressing EPCR in the cells is to upregulate EPCR-dependent anticoagulant or signaling pathways. A preferred way to achieve this is by treating the subject with activated protein (APC) that is engineered to possess APC's signaling properties or its anticoagulant property. Such engineered APC molecules are known in the art. Preferably, the APC is modified as described in the following three references (hereby incorporated by reference) and administered to subjects, preferably systemically or by an intrapulmonary route, such as intrapleurally, in this form (Bae J S et al., Engineering a disulfide bond to stabilize the calcium-binding loop of activated protein C eliminates its anticoagulant but not its protective signaling properties. *J. Biol. Chem.* 282:9251-9259 (2007); Mosnier L O et al., Activated protein C mutant with minimal anticoagulant activity, normal cytoprotective activity, and preservation of thrombin activable fibrinolysis inhibitor-dependent cytoprotective functions. *J. Biol. Chem.* 282:33022-33033 (2007);' Mosnier L O et al., Hyperantithrombotic, noncytoprotective Glu$^{149}$ Ala-activated protein C mutant. *Blood* 113:5970-5978 (2009).

These engineered forms of APC useful in the present methods include variants, as defined herein, of these engineered proteins.

Examples of PAR1 inhibitors that are useful in the present methods are Vorapaxar (SCH530348) and Atopaxar (E5555).

TF inhibitors are known in the art (see, e.g., Weitz, J. et al., New Anticoagulant Drugs—7th Seventh ACCP Conference on Antithrombotic and Thrombolytic Therapy, *Chest* 126:265S-286S (2004), incorporated by reference. TFPI (tissue factor pathway inhibitors) which include active-site inhibited FVIIa ("FVIIai") and tifacogin. Effective doses for TFPI is in the range of about 1 to about 500 μg/kg, preferably between about 10 and about 100 μg/kg, more preferably about 50 μg/kg/Effective doses for FVIIai is between about 1 μg/kg and about 10 mg/kg, more preferably between about 100 μg/kg and about 1 mg/kg, more preferably about, 400 μg/kg.

Downstream Products of the EPCR Pathway

In another embodiment, the present invention is directed to treatment of MPM by administration of any of a number of "downstream products" generated by EPCR pathway that suppress or attenuate cancer progression.

A number of such products are small organic oral anticoagulants that are already in use and/or in clinical trials, such as (1) dabigatran etexilate mesylate, a thrombin inhibitor anticoagulant (Boehringer Ingelheim; Pradaxa®). Preferred daily or twice daily doses of this agent are between about 0.1 and about 500 mg, preferably between about 10 and about 300 mg, more preferably about 150 mg/

(2) rivaroxban, a Factor Xa inhibitor anticoagulant (Janssen Pharmaceuticals, Xarelto®). Preferred daily or twice daily doses of this agent are between about 0.1 and about 100 mg, preferably between about 1 and about 50 mg, more preferably about 15 mg.

STAT3 Inhibitors

Because EPCR attenuates STAT3 activation in MPM cells, the present invention includes used of STAT3 inhibitors to treat MPM. STAT3 is a cytokine transcription factors that has been identified in a number of cancers and participate in cross-talk between signaling pathways. STAT 3 is normally present in all human tissues but is not activated at all times. Once STAT3 is inhibited, the cancer cells will progress to normal cell death or apoptosis. A subject is preferably tested for the presence of STAT 3 in the cancer cells to be treated (or circulating in the blood). A number of small organic molecules that act as STAT-3 inhibitors are known in the art and are in drug development, particularly as anti-cancer agents. Preferred STAT3 inhibitors are OPB-31121 (Otsuka Pharmaceuticals). See: F Hayakawa et al. A novel STAT inhibitor, OPB-31121, has a significant antitumor effect on leukemia with STAT-addictive oncokinases, *Blood Cancer Journal* 3:1-9 ((2013).

GLG 302 from GLG Pharma) which was initially developed as a breast cancer chemopreventive. See, for example, www URL glgpharma.com/glg-pharma-STAT-blog/bid/99370/GLG-302-Selected-by-NCI-for-Funding-in-Cancer-Prevent-Program A preferred daily oral dose for these inhibitors is in the range of about 0.1 to about 200 mg per subject, preferably about 10 to about 100 mg, more preferably, about 50 mg.

By the term "treating" is intended the administering to a subject of a composition comprising a nucleic acid such as the expression vector described herein, a polypeptide or peptide, or small molecule drug alone or in combination. These agents may administered concurrently or sequentially. A pharmaceutical composition comprises such a composition in a pharmaceutically acceptable vehicle. Treatment of cancer or a tumor, preferably MPM by the present method includes the killing, inhibiting or slowing the growth of the relevant target cells, or inhibiting the increase in size of a tumor or cancerous growth. This includes reducing cell numbers, or preventing metastasis. "Treatment" as used herein is not meant to imply or require total cure or disappearance of cancer or a growing tumor. "Treatment" or "treating" is also intended to include prophylaxis, i.e., the prevention of development of a tumor or cancer, either a primary tumor, or more commonly a metastatic tumor or a recurrent tumor at the same or a different site from the primary tumor. For a review of cancer treatment, see any textbook of clinical oncology, e.g., DeVita, V T et al., (eds), *Cancer: Principles and Practice of Oncology*, 7$^{th}$ Edition, Lippincott Williams & Wilkins; 2004).

Also intended is the use of the present methods in conjunction with other conventional cancer treatments, including chemotherapy, radiotherapy, and biotherapy. When used as a supplemental treatment, the method of the present invention, can be initiated before the start of conventional treatment, continued during intervals between subsequent recurring rounds of conventional therapy, and may be continued after cessation of conventional therapy.

Administration of the compositions of the present invention may be by parenteral, subcutaneous (sc), intravenous (iv), intramuscular, intraperitoneal, transdermal routes or, preferably by various intrapulmonary routes including inhalation, lung instillation or by intrapleural administration. Alternatively, or concurrently, administration of compounds or compositions in the present methods may be by the oral route.

The dosage administered will be dependent upon the age, health, and weight of the recipient, kind of concurrent treatment, if any, frequency of treatment, and the nature of the effect desired.

Compositions within the scope of this invention include compositions comprising an EPCR expression vector or EPCR agonist protein, peptide or organic small molecule. The composition is administered in an amount effective to achieve its intended purpose. While individual needs vary, determination of optimal ranges of effective amounts of each component is within the skill of the art. Typical dosages comprise 0.1 to 500 mg/kg/body wt, though more preferred dosages are described for certain particular uses, above and below.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

In addition to a pharmacologically active nucleic acid, protein, peptide or small organic molecule, the present pharmaceutical compositions/preparations preferably contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

The pharmaceutical compositions of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension.

The pharmaceutical formulation for systemic administration according to the invention may be formulated for enteral, parenteral administration or administration by inhalation or lung instillation; and all of these types of formulation may be used simultaneously to achieve systemic administration of the active ingredient.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers the present composition are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The methods of this invention may be used to inhibit growth or metastasis of MPM in a subject in need thereof.

The active nucleic acid/expression vector, protein, peptide or small organic molecule or pharmaceutically acceptable salt thereof is preferably administered in the form of a pharmaceutical composition as described above.

Doses preferably include pharmaceutical dosage units comprising an effective amount of the therapeutic agent. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a regional concentration or a steady state systemic concentration in vivo which results in a measurable reduction in any relevant parameter of disease.

The amount of active compound to be administered depends on the nucleic acid, peptide/polypeptide or small organic molecule that is selected, the state of the disease or condition, the route of administration, the health and weight of the recipient, the existence of other concurrent treatment, if any, the frequency of treatment, the nature of the effect desired, for example, inhibition of primary tumor growth or of metastasis or growth metastatic cell once they have spread, and the judgment of the skilled practitioner.

A preferred single dose, given once daily for treating a subject, preferably a mammal, more preferably human who his suffering from or susceptible to MPM is between about 0.1 mg/kg and about 250 mg/kg, preferably between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

For continuous administration, e.g., by a pump system such as an osmotic pump, a total dosage for a time course of about 1-2 weeks is preferably in the range of 1 mg/kg to 1 g/kg, preferably 20-300 mg/kg, more preferably 50-200 mg/kg. After such a continuous dosing regiment, the total concentration of the peptide is preferably in the range of about 0.5 to about 50 µM, preferably about 1 to about 10 µM.

Effective doses and optimal dose ranges may be determined in vitro or in vivo using methods well-known in the art, including method described herein.

Basic texts disclosing general methods of molecular and cell biology, all of which are incorporated by reference, include: Sambrook, J. et al., *Molecular Cloning: A Laboratory Manual*, 3rd Edition, Cold Spring Harbor Press, N Y, 2001; Green M R and Sambrook, J. eds. *Molecular Cloning: A Laboratory Manual*, 4th Ed, Cold Spring Harbor Press, N Y, 2012; Ausubel, F M et al. *Short Protocols in Molecular Biology*, Vol. 1-2, 5th ed. Current Protocols, New York, (2002 or current edition); Albers, B. et al., *Molecular Biology of the Cell*, $2^{nd}$ Ed., Garland Publishing, Inc., New York, N.Y. (2007); Freshney, *Culture of Animal Cells: A Manual of Basic Technique and Specialized Applications*, 6th ed., Wiley-Blackwell Liss, New York (2010); Krebs, J E et al. Lewin's *GENES XI*, 11th ed., Jones & Bartlett Learning (2012); Watson, J D, et al., *Molecular Biology of the Gene*, 7th ed., Cold Spring Harbor Laboratory Press, 2013; Watson, J D et al., *Recombinant DNA: Genes and Genomes—A Short Course*, $3^{rd}$ Ed., Cold Spring Harbor Laboratory Press, 2007; Lodish, H et al., *Molecular Cell Biology*, 6th ed, W. H. Freeman, New York, N.Y. (2007); Primrose, S B et al. *Principles of Gene Manipulation and Genomics*, 7th Ed., Wiley-Blackwell (2006); Glover, D M, ed., *DNA Cloning: A Practical Approach*, vol. I-III, Oxford Univ. Press, 1987; Nicholl, D S, *An Introduction to Genetic Engineering*, 3rd Ed., Cambridge University Press (2008); Herdewijn, P, *Oligonucleotide Synthesis: Methods and Applications*, Human a Press (2010).

Expression Vectors and Host Cells

This invention includes an expression vector comprising a nucleic acid sequence encoding EPCR and operably linked to at least one regulatory sequence, which includes a promoter that is expressible in a eukaryotic cell, preferably in a mammalian cells, more preferably in a human cell, most preferably in MPM cells.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors may include replicons (e.g., RNA replicons), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and include both the expression and nonexpression plasmids. Where a recombinant cell or culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and/or the type of protein to be expressed. The present expression vectors comprise the full range of nucleic acid molecules encoding the various embodiments of the EPCR polypeptide and its variants and functional derivatives (defined herein)

including homologues, polypeptide fragments, amino acid substitution variants, preferably conservative amino acid substitution variants, addition variants, and deletion variants etc.

The present expression vectors may be used to transfect host cells (in vitro, ex vivo or in vivo) for expression of the DNA and production of the encoded proteins or peptides. It will be understood that a genetically modified cell expressing the EPCR polypeptide may transiently express the exogenous DNA for a time sufficient for the vector and/or cell to be useful for its stated purpose.

Endothelial Protein C Receptor (EPCR) has also been referred to in the literature by other names such as Endothelial Cell Protein C Receptor3, Protein C Receptor (PROCR), Activated Protein C Receptor (APC Receptor), Endothelial CCD41, Cell Cycle Centrosome-Associated Protein, CCCA, centrocyclinand, CD201 antigen.

The coding sequence of EPCR expression vectors of the present vectors is preferably SEQ ID NO:1, including the stop codon. This is the nucleotide (nt) sequence of EPCR coding DNA as disclosed in GenBank Accession No. NM_006404. The underscored portion is the signal peptide.

```
atg ttg aca aca ttg ctg ccg ata ctg ctg ctg tct ggc tgg gcc ttt    48
tgt AGC CAA GAC GCC TCA GAT GGC CTC CAA AGA CTT CAT ATG CTC CAG    96
ATC TCC TAC TTC CGC GAC CCC TAT CAC GTG TGG TAC CAG GGC AAC GCG   144
TCG CTG GGG GGA CAC CTA ACG CAC GTG CTG GAA GGC CCA GAC ACC AAC   192
ACC ACG ATC ATT CAG CTG CAG CCC TTG CAG GAG CCC GAG AGC TGG GCG   240
CGC ACG CAG AGT GGC CTG CAG TCC TAC CTG CTC CAG TTC CAC GGC CTC   288
GTG CGC CTG GTG CAC CAG GAG CGG ACC TTG GCC TTT CCT CTG ACC ATC   336
CGC TGC TTC CTG GGC TGT GAG CTG CCT CCC GAG GGC TCT AGA GCC CAT   384
GTC TTC TTC GAA GTG GCT GTG AAT GGG AGC TCC TTT GTG AGT TTC CGG   432
CCG GAG AGA GCC TTG TGG CAG GCA GAC ACC CAG GTC ACC TCC GGA GTG   480
GTC ACC TTC ACC CTG CAG CAG CTC AAT GCC TAC AAC CGC ACT CGG TAT   528
GAA CTG CGG GAA TTC CTG GAG GAC ACC TGT GTG CAG TAT GTG CAG AAA   576
CAT ATT TCC GCG GAA AAC ACG AAA GGG AGC CAA ACA AGC CGC TCC TAC   624
ACT TCG CTG GTC CTG GGC GTC CTG GTG GGC AGT TTC ATC ATT GCT GGT   672
GTG GCT GTA GGC ATC TTC CTG TGC ACA GGT GGA CGG CGA TGT taa       714
```

The above sequence showing the encoded amino acid sequence (in single letter code (SEQ ID NO:2), is shown below:

```
atg ttg aca aca ttg ctg ccg ata ctg ctg ctg tct ggc tgg gcc ttt    48
 M   L   T   T   L   L   P   I   L   L   L   S   G   W   A   F tgt AGC CAA GAC GCC TCA GAT GGC CTC CAA AGA CTT CAT ATG CTC CAG    96
 C   S   Q   D   A   S   D   G   L   Q   R   L   H   M   L   Q ATC TCC TAC TTC CGC GAC CCC TAT CAC GTG TGG TAC CAG GGC AAC GCG   144
 I   S   Y   F   R   D   P   Y   H   V   W   Y   Q   G   N   A TCG CTG GGG GGA CAC CTA ACG CAC GTG CTG GAA GGC CCA GAC ACC AAC   192
 S   L   G   G   H   L   T   H   V   L   E   G   P   D   T   N ACC ACG ATC ATT CAG CTG CAG CCC TTG CAG GAG CCC GAG AGC TGG GCG   240
 T   T   I   I   Q   L   Q   P   L   Q   E   P   E   S   W   A CGC ACG CAG AGT GGC CTG CAG TCC TAC CTG CTC CAG TTC CAC GGC CTC   288
 R   T   Q   S   G   L   Q   S   Y   L   L   Q   F   H   G   L GTG CGC CTG GTG CAC CAG GAG CGG ACC TTG GCC TTT CCT CTG ACC ATC   336
 V   R   L   V   H   Q   E   R   T   L   A   F   P   L   T   I CGC TGC TTC CTG GGC TGT GAG CTG CCT CCC GAG GGC TCT AGA GCC CAT   384
 R   C   F   L   G   C   E   L   P   P   E   G   S   R   A   H GTC TTC TTC GAA GTG GCT GTG AAT GGG AGC TCC TTT GTG AGT TTC CGG   432
 V   F   F   E   V   A   V   N   G   S   S   F   V   S   F   R CCG GAG AGA GCC TTG TGG CAG GCA GAC ACC CAG GTC ACC TCC GGA GTG   480
 P   E   R   A   L   W   Q   A   D   T   Q   V   T   S   G   V
```

```
GTC ACC TTC ACC CTG CAG CAG CTC AAT GCC TAC AAC CGC ACT CGG TAT        528
 V   T   F   T   L   Q   Q   L   N   A   Y   N   R   T   R   Y

GAA CTG CGG GAA TTC CTG GAG GAC ACC TGT GTG CAG TAT GTG CAG AAA        576
 E   L   R   E   F   L   E   D   T   C   V   Q   Y   V   Q   K

CAT ATT TCC GCG GAA AAC ACG AAA GGG AGC CAA ACA AGC CGC TCC TAC        624
 H   I   S   A   E   N   T   K   G   S   Q   T   S   R   S   Y

ACT TCG CTG GTC CTG GGC GTC CTG GTG GGC AGT TTC ATC ATT GCT GGT        672
 T   S   L   V   L   G   V   L   V   G   S   F   I   I   A   G

GTG GCT GTA GGC ATC TTC CTG TGC ACA GGT GGA CGG CGA TGT taa            714
 V   A   V   G   I   F   L   C   T   G   G   R   R   C   *
```

The preferred full-length EPCR amino acid sequence (in single letter code), SEQ ID NO:2 shown below

```
MLTTLLPILL LSGWAFCSQD ASDGLQRLHM LQISYFRDPY HVWYQGNASL        50

GGHLTHVLEG PDTNTTIIQL QPLQEPESWA RTQSGLQSYL LQFHGLVRLV       100

HQERTLAFPL TIRCFLGCEL PPEGSRAHVF FEVAVNGSSF VSFRPERALW       150

QADTQVTSGV VTFTLQQLNA YNRTRYELRE FLEDTCVQYV QKHISAENTK       200

GSQTSRSYTS LVLGVLVGSF IIAGVAVGIF LCTGGRRC                   238
```

Also included in the invention are variants of the above nucleic acid for encoding the same amino acid sequence based on degeneracy of the genetic code.

The coding sequence (or non-coding sequence) of the nucleic acids useful herein preferably are codon-optimized for the species in which they are to be expressed, most particularly, humans. Such codon-optimization is routine in the art.

Preferred nt sequence variants of SEQ ID NO:1, include fragments, sequence encoding substitution variants, preferably conservative amino acid substitution variants, and/or addition variants, which collectively are referred to as "functional derivatives."

The preferred nucleic acid sequence variants of the present invention have the following degrees of sequence identity with SEQ ID NO:1: about 50%, about 55%, about 60%, about 65%, about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, such as, for example, from about 70% to about 80%, and more preferably from about 81% to about 90%; or even more preferably, from about 91% to about 99% identity.

While a preferred vector comprising a transgene encodes a full length polypeptide, preferably EPCR (SEQ ID NO:2, as indicated, the present invention is also directed to vectors that encode a biologically active fragment or a conservative amino acid substitution variant or an addition variant of EPCR (or other polypeptide of the invention) to be delivered to or expressed in lungs.

The homologue, fragment or variant is expressed by targets cells in the subject being transduced with EPCR and is able to lead to death of MPM cells or to endow such cells with heightened susceptibility to killing by endogenous, or exogenously administered IFNγ and/or TNFα, that is functionally equivalent to that of the full length or substantially full length EPCR polypeptide having a native, rather than variant, amino acid sequence. A biologically active fragment or variant is a "functional equivalent"—a term that is well understood in the art and is further defined in detail herein.

The requisite biological activity of the fragment or variant, using any method disclosed herein or known in the art has the following activity relative to the wild-type native polypeptide of at least about: 20%, 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably, from about 91% to about 99%.

It should be appreciated that any variations in the coding sequences of the present nucleic acids and vectors that, as a result of the degeneracy of the genetic code, express a polypeptide of the same sequence, are included within the scope of this invention.

The amino acid sequence identity of the variants of the present invention are determined using standard methods, typically based on certain mathematical algorithms. In a preferred embodiment, the percent identity between two amino acid sequences is determined using the Needleman and Wunsch (J. Mol. Biol. 48:444-453 (1970) algorithm which has been incorporated into the GAP program in the GCG software package (available at WWW URL gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the WWW web address gcg.com, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (CABIOS 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) J. Mol. Biol. 215:403-10). BLAST nucleotide searches can be performed with the NBLAST program, score=100, wordlength=12 to obtain homologous nucleotide sequences. BLAST protein searches can be performed with the)(BLAST program, score=50, wordlength=3 to obtain amino acid sequences homologous to the appropriate reference protein. To obtain gapped alignments for comparison purposes, Gapped BLAST can be utilized (Altschul et al. (1997) *Nucleic Acids Res.* 25:3389-3402). When utilizing BLAST and Gapped BLAST programs, the default parameters of the respective programs (e.g., XBLAST and NBLAST) can be used. See World Wide Web URL ncbi.nlm.nih.gov.

The preferred amino acid sequence variant has the following degrees of sequence identity with the native, full length EPCR (SEQ ID NO:2) about 50%, about 55%, about 60%, about 65%, about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, such as, for example, from about 70% to about 80%, and more preferably from about 81% to about 90%; or even more preferably, from about 91% to about 99% identity.

Preferred substitutions variants of the proteins and peptides of this invention are conservative substitutions in which 1, 2, 3, 4, 5, 6, 7, 8, 9, 10, 11, 12, 13, 14, 15, 16, 17, 18, 19, 20, 11-25, 26-30, 31-35, 36-40, 41-45 or 45-50 amino acid residues have been substituted by different residue. Most preferably less than 20, more preferably less than 10, and most preferably 5 or fewer residues are substituted. For a detailed description of protein chemistry and structure, see Schultz G. E. et al., *Principles of Protein Structure*, Springer-Verlag, New York, 1979, and Creighton, T. E., *Proteins: Structure and Molecular Properties*, $2^{nd}$ ed., W.H. Freeman & Co., San Francisco, 1993, which are hereby incorporated by reference. Conservative substitutions and are defined herein as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;
4. Large aliphatic, nonpolar residues: Met, Leu, Ile, Val (Cys); and
5. Large aromatic residues: Phe, Tyr, Trp.

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Preferred substitutions according to the present invention are those which do not produce radical changes in the characteristics of the polypeptide molecule. Most acceptable deletions and insertions (addition variants) according to the present invention are those which do not produce radical changes in the characteristics of the protein or peptide.

Even when it is difficult to predict the exact effect of a substitution in advance of doing so, one skilled in the art will appreciate that the effect can be evaluated by routine screening assays, preferably the biological and biochemical assays described herein. The activity of a cell lysate or purified polypeptide or peptide variant is screened in a suitable screening assay for the desired characteristic. For example, a change in the immunological characteristic of the polypeptide or peptide molecule is assayed by alterations in binding to a given antibody, and is measured by an immunoassay. Biological activity is screened in an appropriate bioassay, as described herein or known in the art. When appropriate, measurement of receptor-ligand binding is a way to screen a variant for its biochemical or functional properties. Modifications of polypeptide properties such as redox or thermal stability, hydrophobicity, susceptibility to proteolytic degradation or the tendency to aggregate with carriers or into multimers are assayed by methods well known to the ordinarily skilled artisan.

Certain commonly encountered "non-standard" amino acids well-known in the art can be substituted for standard amino acids. These include, for example, include β-alanine (β-Ala) and other ω-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); norleucine (Nle); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); homoarginine (hArg); N-acetyl lysine (AcLys); 2,4-diaminobutyric acid (Dbu); 2,4-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

Covalent modifications of the polypeptides are included and may be introduced by reacting targeted amino acid residues with an organic derivatizing agent that is capable of reacting with selected side chains or terminal residues.

Such chemically modified and derivatized moieties may improve a polypeptide's or peptide's solubility, absorption, biological half life, and the like. These changes may eliminate or attenuate undesirable side effects of the polypeptides in vivo. Moieties capable of mediating such effects are disclosed, for example, in Gennaro, A R, *Remington: The Science and Practice of Pharmacy*, Lippincott Williams & Wilkins Publishers; $21^{st}$ Ed, 2005 (or latest edition)

Any of a number of known recombinant methods are used to produce a DNA molecule encoding the polypeptide fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, *DNA* 2:183-93). These mutations include simple deletions or insertions, systematic deletions, insertions or substitutions of clusters of bases or substitutions of single bases.

The present in invention provides methods for producing the polypeptides, fragments and derivatives. For example, a host cell transfected with a nucleic acid vector that encodes the fusion polypeptide is cultured under appropriate conditions to allow expression of the polypeptide.

Host cells may also be transfected with one or more expression vectors that singly or in combination comprise DNA encoding at least a portion of the EPCR polypeptide.

If desired, the polypeptide can be isolated from medium or cell lysates using conventional techniques for purifying proteins and peptides, including ammonium sulfate precipitation, fractionation column chromatography (e.g., ion exchange, gel filtration, affinity chromatography, etc.) and/or electrophoresis (see generally, *Meth Enzymol,* 22:233-577 (1971)). Once purified, partially or to homogeneity, the recombinant polypeptides of the invention can be utilized in pharmaceutical compositions as described in more detail herein.

The term "isolated" as used herein, when referring to a molecule or composition, such as a polypeptide or a nucleic acid, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contaminants which co-purify with it.

Host cells transfected or transduced to express the EPCR polypeptide or a variant, homologue or functional derivative thereof are within the scope of the invention. For example, the polypeptide may be expressed in yeast, or mammalian cells such as Chinese hamster ovary cells (CHO) or, preferably human cells. Preferred cells for expression according to the present invention are MPM cells. Other suitable host cells are known to those skilled in the art. Expression in eukaryotic cells leads to partial or complete glycosylation and/or formation of relevant inter- or intra-chain disulfide bonds of the recombinant protein.

Often, in expression vectors, a nucleotide sequence encoding a proteolytic cleavage site is introduced at the junction of the reporter group and the target protein to enable their separation after to purification of the expressed protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs) and pRIT5 (Pharmacia, Piscataway, N.J.) which fuse glutathione S-transferase, maltose E binding protein, or protein A, respectively, to the target recombinant protein. Inducible expression vectors include pTrc (Amann et al., *Gene* 69:301-15, 1988) and pET 11d (Studier et al., *Gene Expression Technology: Meth Enzymol* 185:60-89, 1990).

Vector Construction

Construction of suitable vectors comprising the desired coding and control sequences employs standard ligation and restriction techniques which are well understood in the art. Isolated plasmids, DNA sequences, or synthesized oligonucleotides are cleaved, tailored, and re-ligated in the form desired.

Nucleic acids can also be chemically synthesized using standard techniques, including solid-phase synthesis which, like peptide synthesis, has been fully automated with commercially available DNA synthesizers (Itakura U.S. Pat. Nos. 4,598,049, 4,401,796 and 4,373,071; Caruthers et al. U.S. Pat. No. 4,458,066.).

The DNA sequences which form the vectors of the invention or vectors using during production of the nucleic acids of the invention are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully. Synthetic oligonucleotides are prepared by either the phosphotriester method as described by references cited above or the phosphoramidite method (Beaucage, S L et al., *Tet Lett* 22:1859, 1981; Matteucci, M D et al., *J Am Chem Soc* 103:3185, 1981) using commercially available automated oligonucleotide synthesizers. Once the components of the desired vectors are thus available, they can be excised and ligated using standard restriction and ligation procedures. Site-specific DNA cleavage is performed by treating with the suitable restriction enzyme or enzymes under conditions which are conventional in the art, the particulars of which are specified by the manufacturer of commercially available restriction enzymes. See, e.g., New England Biolabs, Product Catalog; *Meth Enzymol.* 65:499-560, 1980.

Any of a number of methods are used to introduce mutations into the coding sequence to generate the variants of the invention. These mutations include simple deletions or insertions, systematic deletions, insertions or substitutions of clusters of bases or substitutions of single bases. For example, modifications of DNA sequences are created by site-directed mutagenesis, a well-known technique for which protocols and reagents are commercially available (Zoller, M J et al., *Nucleic Acids Res* 10:6487-500, 1982; Adelman, J P et al., *DNA* 2:183-193, 1983). Using conventional methods, transformants are selected based on the presence of a selectable marker such as an antibiotic resistance gene depending on the mode of plasmid construction.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The promoter sequences of the present invention must be operable in mammalian cells and may be either eukaryotic or viral promoters. While, preferred promoters are described below, other useful promoters and regulatory elements are also discussed. Suitable promoters may be inducible, repressible or constitutive, most preferably constitutive and tissue- or cell type-specific. A "constitutive" promoter is one which is active under most conditions encountered in the cell's environmental and throughout development. An "inducible" promoter is one which is under environmental or developmental regulation. A "tissue specific" or cell type-specific promoter is active in certain tissues or cell types of an organism.

An example of a constitutive promoter is the viral promoter MSV-LTR, which is efficient and active in a variety of cell types, and, in contrast to most other promoters, has the same enhancing activity in arrested and growing cells. Other viral promoters include that present in the CMV-LTR (from cytomegalovirus) (Bashart, M. et al., *Cell* 41:521, 1985) or in the RSV-LTR (from Rous sarcoma virus) (Gorman, C. M., *Proc. Natl. Acad. Sci. USA* 79:6777, 1982). Also useful are the promoter of the mouse metallothionein I gene (Hamer, D, et al., *J. Mol. Appl. Gen.* 1:273-88, 1982; the TK promoter of Herpes virus (McKnight, S, *Cell* 31:355-65, 1982); the SV40 early promoter (Benoist, C., et al., *Nature* 290:304-10, 1981); and the yeast gal4 gene promoter (Johnston, S A et al., *Proc. Natl. Acad. Sci. USA* 79:6971-5, 1982); Silver, P A, et al., *Proc. Natl. Acad. Sci.* (USA) 81:5951-5, 1984)). Other illustrative descriptions of transcriptional factor association with promoter regions and the separate activation and DNA binding of transcription factors include: Keegan et al., *Nature* 231:699, 1986; Fields et al., *Nature* 340:245, 1989; Jones, *Cell* 61:9, 1990; Lewin, *Cell* 61:1161, 1990; Ptashne et al., *Nature* 346:329, 1990; Adams et al., *Cell* 72:306, 1993.

The promoter region may further include an octamer region which may also function as a tissue specific enhancer, by interacting with certain proteins found in the specific tissue. The enhancer domain of the DNA construct of the present invention is one which is specific for the target cells to be transfected, preferably MPM cells, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, for example Lewin's *GENES XI*, supra. Retroviral enhancers (e.g., viral LTR) may be used and are preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

The most preferred promoters and enhancers for the present invention are MPM-specific promoters. One example is the promoter of the gene for CREB-BP/EP300 inhibitor 1 (CRI1) (also known as EID-1) (Gordon, G J et al., *Am. J. Pathol.* 166:1827-40) (2005); Gordon, G J. et al., *Clin Cancer Res* 11:4406-14) (2005). CRI1 is a CREB-binding protein and potential oncogene that, in functional assays, antagonizes the action of pRb, p300, and CREB-binding protein (CBP) histone acetylase activity (Miyake S et al., *Mol Cell Biol* 2000, 20:8889-8902). CRI1 binds and sequesters wild-type unphosphorylated (active) pRb, but also acts at points downstream of pRb in differentiation and proliferation control pathways. These observations are particularly notable in the context of mesothelioma because, many MPMs are found to have deletions, mutations, or promoter methylation of p16INK4a (a regulator of pRb via inhibitory action on cdk4). This promoter is exclusively expressed in MPM cells and not in normal mesothelial cells or fibroblasts (Fukazawa T et al., "Malignant pleural mesothelioma-targeted CREBBP/EP300 inhibitory protein 1 promoter system for gene therapy and virotherapy." *Cancer Res.* 68:7120-29 (2008), incorporated by reference. The promoter sequence (described in the foregoing 3 references or reference cited therein) was particularly potent when 4 copies were arranged in tandem.

Another preferred promoter and promoter/enhancer combination is the mesothelin gene promoter that is highly expressed in aggressive mesotheliomas and other cancers (Hassan R, Bera T, Pastan I, *Clin Cancer Res* 10:3937-3947 (2004). Sequences of the promoter are shown in Hucl, T et al., "High Cancer-Specific Expression of Mesothelin (MSLN) is Attributable to an Upstream Enhancer Containing a Transcription Enhancer Factor-Dependent MCAT Motif," *Cancer Res* 67:9055-9065 (2007) FIG. 1D of Hucl et al. shows a sequence of the 5'-end of the mesothelin (MSLN) gene (SEQ ID NO:3, below), including the underscored MSLN promoter sequence (SEQ ID NO:4). Shown in the sequence below are 10 different possible transcriptional start sites, 3 corresponding to the consensus initiator sequence (overlying arrows), the rest to nonconsensus start sites (overlying arrowheads). The lower case region is a cryptic intron excised at cryptic splice sites that define the borders of alternate exons 1A and 1B. (The translation start site of the gene, in exon 2, is not shown). The final 2 nt's are the:start of intron 1. Double underlined, italics are two distinct functional sites of the enhancer element (see FIG. 4A of Hucl et al., supra.

SEQ ID NO: 3

```
CCTCCCCCAGGCCTGGCCCGCTGCCTGTCCAAGGCTCCTGTGCGGGGTCTCCACCCAC
ACATTCCTGGGGCGTGAGGCGCCACCACTCCCTGCTCCCCGGGCAAAGCCGCTCATTT
GTTCCCTTTGACGGCCCGGGAGGCTGCCAGGCTCTCCACCCCCACTTCCCAATTGAGG
AAACCGAGGCAGAGGAGGCTCAGgtgtggccaatcaccctgcacatcagagttaccct
gggcagggcccactgagacctgggaggggccactcgggacctggagggctggggctg
cccgggcgttaggggtaaagctccctacccaactgcgcagaaggcctcagaggcctgg
gggctgggcttcccctttcacatcgcccttagaggcccacgtgtgggcattggcccg
cgatctgaaaggggctgtcctgttcctcatgggcgctgccagCGCCACGCACTCCTCT
TTCTGCCTGGCCGGCCACTCCCGTCTGCTGTGACGCGCGGACAGAGAGCTACCGGTGG
ACCCACGGTGCCCTCCCCTCCCTCCCTGGGATCTGT
```

(from the MSLN UTR)

SEQ ID NO: 4

```
ATTTGTTCCC TTTGACGGCC CGGGAGGCTG CCAGGCTCTC CACCCCCACT
TCCCAATTGA GGAAACCGAG GCAGAGGAGG CTCAGG
```

Delivery of DNA Encoding EPCR Polypeptide

DNA delivery to animals, for example to effect what is generally known as "gene therapy," or to cells ex vivo, involves introduction of a "foreign" DNA into a cell and ultimately, into a live animal. As used herein, the term "gene therapy" is not intended to be limited to the correction or replacement of a deficient gene in vivo, rather, the delivery of a polynucleotide, preferably a DNA molecule, of the present invention (not necessarily a "gene") in a manner permitting it expression and thereby, its utility as described. Several general strategies for gene therapy have been studied and have been reviewed extensively (Yang, N-S, *Crit Rev Biotechnol* 12:335-56 (1992); Anderson, W F, *Science* 256:808-13 (1992); Miller, A S, *Nature* 357:455-60 (1992); Crystal, R G, *Amer. J. Med.* 92(suppl 6A):445-525 (1992); Zwiebel, J A et al., *Ann. N.Y. Acad. Sci.* 618:394-404 (1991); McLachlin, J R et al., *Prog Nucl Acid Res Molec Biol* 38:91-135 (1990); Kohn, D B et al., *Cancer Invest.* 7:179-92 (1989), which references are herein incorporated by reference in their entirety).

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Green and Sambrook, supra and other standard texts. One approach comprises nucleic acid transfer into primary cells in culture followed by autologous transplantation (implantation) of the ex vivo transformed cells into the host, either systemically or into a particular organ or tissue.

For accomplishing the objectives of the present invention, nucleic acid therapy would be accomplished by direct transfer of a functionally active, expressible, DNA molecule into the target tissue or cells in vivo. DNA transfer can be achieved using a number of approaches described below. These systems can be tested for successful expression in vitro by use of a selectable marker (e.g., G418 resistance) to select transfected clones expressing the DNA, followed by detection of the presence of the EPCR expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

While preferred means for transfer of nucleic acid into cells for expression (also referred to as "transduction") are provide in the Examples below, other methods of successful transfer include: (a) direct injection of plasmid DNA into muscle tissues, which led to expression of marker genes for an indefinite period of time (Wolff, J A et al., *Science* 247:1465 (1990); (b) retroviral vectors are effective for in vivo and in situ infection of blood vessel tissues; (c) portal vein injection and direct injection of retrovirus preparations into liver effected gene transfer and expression in vivo (Horzaglou, M et al., *J Biol Chem* 265:17285 (1990); Ferry, N et al., *Proc Natl Acad Sci USA* 88:8387 (1991)); (d) intratracheal infusion of recombinant adenovirus into lung tissues was effective for in vivo transfer and prolonged expression of foreign genes in respiratory epithelium (Rosenfeld, M A et al., *Science* 252:431 (1991); (e) Herpes simplex virus vectors achieved in vivo DNA transfer into brain tissue (Ahmad, F et al., eds, *Advances in Gene Technology: The Molecular Biology of Human Genetic Disease*, Vol 1, Boehringer Mannheim Biochemicals, USA, 1991).

Retroviral-mediated human therapy utilizes amphotrophic, replication-deficient retrovirus systems (Temin, H M, *Hum Gene Ther* 1:111 (1990); Temin et al., U.S. Pat. Nos. 4,980,289, 4,650,764, and 5,124,263; Wills, J W, U.S. Pat. No. 5,175,099; Miller, A D, U.S. Pat. No. 4,861,719). Such vectors have been used to introduce functional DNA into human cells or tissues, for example, the adenosine deaminase gene into lymphocytes, the NPT-II gene and the gene for TNFα into tumor infiltrating lymphocytes. Retrovirus-mediated gene delivery generally requires target cell proliferation for gene transfer (Miller, D G et al., *Mol Cell Biol.* 10:4239 (1990). This condition is met by certain target cells, i.e., actively growing tumor cells.

The DNA molecules encoding EPCR polypeptide sequences may be packaged into retrovirus vectors using packaging cell lines that produce replication-defective retroviruses, as is well-known in the art (see, for example, Miller, A D et al., *Mol. Cell Biol.* 5:431-37 (1985). Additional safe and effective packaging cell lines for gene transfer are described in, e.g., U.S. Pat. No. 5,278,056. This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor. Advantages of adenovirus vectors for human gene therapy include the fact that recombination is rare, no human malignancies are known to be associated with such viruses, the ds DNA adenovirus genome can be manipulated to accept foreign genes of up to 7.5 kb in size, and live adenovirus is a safe for use in humans. *Fields Virology* (D. M. Knipe et al., eds), 6$^{th}$ ed. Lippincott Williams & Wilkins (2013), Wold, W S et al. eds, *Adenovirus Methods and Protocols*: Vols 1 and 2, 2$^{nd}$ ed., Humana Press, 2007; Berkner, K L (1992) *Curr Top Microbiol Immunol* 158:39-66).

Adeno-associated virus (AAV) is also useful for human therapy (Samulski, R J et al., *EMBO J.* 10:3941 (1991) and is within the scope of this invention. AAVs are small, single-stranded DNA viruses which require a helper virus for efficient replication (*Fields Virology*, supra; Kerr, J. et al., *Parvoviruses*, 1$^{st}$ ed., CRC Press (2005); Tijssen, P, CRC Handbook of Parvoviruses, Vols. 1-2, CRC Press, 1989. The 4.7 kb genome of AAV has two inverted terminal repeats (ITR) and two open reading frames (ORFs) which encode the Rep proteins and Cap proteins, respectively. The Rep reading frame encodes four proteins of molecular weights 78, 68, 52 and 40 kDa. These proteins primarily function in regulating AAV replication and rescue and integration of the AAV into the host cell chromosomes. The Cap reading frame encodes three structural proteins of molecular weights 85 (VP 1), 72 (VP2) and 61 (VP3) kDa which form the virion capsid (Berns, supra). VP3 comprises >80% of total AAV virion proteins. Flanking the rep and cap ORFs at the 5' and 3' ends are 145 bp ITRs, the first 125 bp's of which can form Y- or T-shaped duplex structures. The two ITRs are the only cis elements essential for AAV replication, rescue, packaging and integration of the genome. Two conformations of AAV ITRs called "flip" and "flop" exist (Snyder, R O et al., 1993, *J Virol.*, 67:6096-6104; Berns, K I, 1990 *Microbiol Rev,* 54:316-29). The entire rep and cap domains can be excised and replaced with a transgene such as a reporter or therapeutic transgene (Carter, B J, in P. Tijsser, supra). AAVs have been found in many animal species, including primates, canine, fowl and human (Murphy, F A et al., *The Classification and Nomenclature of Viruses: Sixth Rept of* the Int'l Comm on Taxonomy of Viruses, Arch Virol, Springer-Verlag, 1995). Six primate serotypes are known (AAV1, AAV2, AAV3, AAV4, AAV5 and AAV6).

The AAV ITR sequences and other AAV sequences employed in generating minigenes, vectors, and capsids, and other constructs that are used in the present invention may be obtained from a variety of sources. For example, the sequences may be provided by any of the above 6 AAV serotypes or other AAV serotypes or other densoviruses, including both presently known human AAV and yet to yet-to-be-identified serotypes. Similarly, AAVs known to infect other animal species may be the source of ITRs used in the present molecules and constructs. Capsids from a variety of serotypes of AAV may be combined in various mixtures with the other vector components (e.g., WO2001/83692 incorporated by reference). Many of these viral strains or serotypes are available from the American Type Culture Collection (ATCC), Manassas, Va., or from a variety of academic or commercial sources.

It may be desirable to synthesize sequences used in preparing the vectors of the invention using known techniques, based on published AAV sequences, e.g., available from a variety of databases. The source of the sequences utilized to prepare the present constructs is not considered to be limiting. Similarly, the selection of the AAV serotype and species (of origin) is within the skill of the art and is not considered limiting As used herein, the AAV sequences are typically in the form of a rAAV construct (e.g., a minigene or cassette) which is packaged into a rAAV virion. At minimum, the rAAV minigene is formed by AAV ITRs and a heterologous nucleic acid molecule for delivery to a host cell. Most suitably, the minigene comprises ITRs located 5' and 3' to the heterologous sequence. However, minigene comprising 5' ITR and 3' ITR sequences arranged in tandem, e.g., 5' to 3' or a head-to-tail, or in another configuration may also be desirable. Other embodiments include a minigene with multiple copies of the ITRs, or one in which 5' ITRs (or conversely, 3' ITRs) are located both 5' and 3' to the heterologous sequence. The ITRs sequences may be located immediately upstream and/or downstream of the heterologous sequence; intervening sequences may be present. The ITRs may be from AAV5, or from any other AAV serotype. A minigene may include 5' ITRs from one serotype and 3' ITRs from another.

The AAV sequences used are preferably the 145 bp cis-acting 5' and 3' ITR sequences (e.g., Carter, supra). Preferably, the entire ITR sequence is used, although minor modifications are permissible. Methods for modifying these ITR sequences are well-known (e.g., Green and Sambrook, supra; Ausubel, et al., supra; Carter Fisher, K et al., 1996 *J Virol.* 70:520-32). It is conventional to engineer the rAAV virus using known methods (e.g., Bennett, J et al. 1999, supra). An example of such a molecule employed in the present invention is a "cis-acting" plasmid containing the heterologous sequence, preferably the Chop2 sequence, flanked by the 5' and 3' AAV ITR sequences.

The heterologous sequence encodes a protein or polypeptide which is desired to be delivered to and expressed in a cell. The present invention is directed to EPCR sequences under the control of a selected promoter and other vector regulatory components.

In a preferred embodiment, the heterologous sequence is a nucleic acid molecule that functions as a transgene. The term "transgene" as used herein refers to a nucleic acid sequence heterologous to the AAV sequence, and encoding a desired product, preferably EPCR and regulatory sequences which direct or modulate transcription and/or translation of this nucleic acid in a host cell, preferably MPM cells, enabling expression in such cells of the encoded product (in vitro or in vivo). Preferred polypeptide products are those that can be delivered to the lungs. The transgene is delivered and expressed in order to induce killing or inhibition of proliferation of MPM cells in the treatment of MPM.

Different transgenes may be used to encode separate subunits of the protein being delivered, or to encode different polypeptides the co-expression of which is desired. If a single transgene includes DNA encoding each of several subunits, the DNA encoding each subunit may be separated by an internal ribozyme entry site (IRES), which is preferred for short subunit-encoding DNA sequences (e.g., total DNA, including IRES is <5 kB). Other methods which do not employ an IRES may be used for co-expression, e.g., the use of a second internal promoter, an alternative splice signal, a co- or post-translational proteolytic cleavage strategy, etc., all of which are known in the art.

Vaccinia virus which can be rendered non-replicating can express the DNA molecule of the present invention and is useful in humans (U.S. Pat. Nos. 5,225,336; 5,204,243; 5,155,020; 4,769,330; Sutter, G et al., *Proc Natl Acad Sci USA* (1992) 89:10847-51; Fuerst, T R et al., *Proc Natl Acad Sci USA* (1989) 86:2549-2553; Falkner F G et al.; *Nucl Acids Res* (1987) 15:7192; Chakrabarti, S et al., *Molec Cell Biol* (1985) 5:3403-3409). Descriptions of recombinant vaccinia viruses and other viruses containing heterologous DNA and their uses are reviewed in Moss, B, *Curr Opin Genet Dev* (1993) 3:86-90; Moss, B, *Biotechnology* (1992) 20: 345-62; Moss, B, *Curr Top Microbiol Immunol* (1992) 158:25-38; Moss, B, *Science* (1991) 252:1662-67; Piccini, A et al., *Adv Vir Res* (1988) 34:43-64; and Moss, B et al., *Gene Amplif Anal* (1983) 3:201-13.

In addition to naked DNA or RNA, or viral vectors, engineered bacteria may be used as vectors, for example, any of a number of bacterial species including *Salmonella*, BCG and *Listeria monocytogenes* (LM) (Hoiseth et al., *Nature* 291:238-39 (1981); Poirier, T P et al. *J Exp Med* 168:25-32 (1988); Sadoff, J C, et al., *Science* 240:336-38 (1988); Stover, C K et al., *Nature* 351:456-60 (1991); Aldovini, A. et al., *Nature* 351:479-82 (1991); Schafer, R. et al., *J. Immunol.* 149:53-9 (1992); Ikonomidis, G. et al., *J Exp Med* 180:2209-18 (1994)). The enteric routes of infection of such organisms has a promising characteristic for their use because they may be delivered orally.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N-S, et al., *Proc Natl Acad Sci USA* 87:9568 (1990); Williams, R S et al., *Proc Natl Acad Sci USA* 88:2726 (1991); Zelenin, A V et al., *FEBS Lett.* 244:65 (1989) and *FEBS Lett.* 280:94 (1991); Zelenin, A V et al., *FEBS Lett.* 244:65 (1989); Johnston, S A et al., In *Vitro Cell Dev Bio.* 27:11 (1991)). Furthermore, electroporation, a well-known means to transfer genes into cell in vitro, can be used to transfer DNA molecules according to the present invention to tissues in vivo (Titomirov, A V et al., *Biochim Biophys Acta* 1088:131 ((1991))

"Carrier mediated" gene transfer (or DNA delivery) has also been described (Wu, C H et al., *J Biol Chem.* 264:16985 (1989); Wu, G Y et al., *J Bio. Chem* 263:14621 (1988); Soriano, P et al., *Proc Natl Acad Sci USA* 80:7128 (1983); Wang, C Y. et al., *Proc Natl Acad Sci USA* 84:7851 (1982); Wilson, J M et al., *J Biol Chem* 267:963 (1992)). Preferred carriers are targeted liposomes (Nicolau, C. et al., *Proc Natl Acad Sci USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Qiagen procedure (Qiagen), followed by DNA purification using known methods, such as the methods exemplified herein.

Again, as noted above, for the utility of transduced EPCR molecules according to this invention may not always require stable or prolonged expression. Rather, transient expression of the polypeptide may be sufficient for certain of the desired effects on transduced MPM cells.

Having now generally described the invention, the same will be more readily understood through reference to the following examples which are provided by way of illustration, and are not intended to be limiting of the present invention, unless specified.

EXAMPLE I

Materials and Methods

Cell Lines and Reagents

REN cells were from S. Albelda, University of Pennsylvania, MS-1 cells were from S-M. Hsu, University of Texas Health Science Center at Houston, and M9K cells were from Dr. B. Gerwin, NIH. All cells were grown in RPMI medium+10% fetal bovine serum and 1% penicillin/streptomycin. Preparation of monospecific polyclonal anti-human TF IgG was described earlier (32). EPCR antibodies were obtained from C. T. Esmon, Oklahoma Medical Research Foundation. PAR1 and PAR2 antibodies were from Santa Cruz Biotechnology (Santa Cruz, Calif.). PAR1 and PAR2 agonist peptides were from Biosynthesis, Lewisville, Tex. Recombinant human FVIIa was obtained from Novo Nordisk (Maaloev, Denmark). Factor X was obtained from Enzyme Research Laboratories (South Bend, Ind.).

Generation of Stable Transfectants of MPM Cells Expressing/Lacking TF, EPCR or PAR1

TF or PAR1 expression in REN MPM cells was selectively knocked-down by shRNA. shRNA clones were generated using pSilencer 2.1 U6 puro vector kits (Ambion, Austin Tex.). The seed sequences of oligonucleotides used for knock-down of TF gene were, GAAGCAGACGTACTTGGCA (SEQ ID NO:5) and GCGCTTCAGGCACTACAAAT (SEQ ID NO:6), for knock-down of PAR1 gene was AGGCTCTACTATGCCTACTACT (SEQ ID NO:7). Double stranded DNA was designed essentially following the instructions given in the protocol supplied with the kit. The annealed double stranded DNA was ligated into the cloning site BamH1 and Hind III cloning site of the precut vector from the kit. Sequences of shRNA plasmid constructs were confirmed before transfecting them into tumor cells. A day after the seeding, REN cells cultured in 6-well plate were transfected with 4 µg pSilencer 2.1 U6-Puro expression plasmid containing either TF, PAR1 or control shRNA sequence using Fugene HD reagent (Promega, WI) at 3:2 ratio. Two days after transfection, cells were placed in complete RPMI medium containing puromycin (1 µg/ml). Individual colonies were then selected, expanded and evaluated for TF expression and PAR1 expression by measuring cell surface TF activity in factor X activation assay and intracellular $Ca^{2+}$ release in response to PAR1 agonist peptide, respectively. Stable transfectants of PAR1 knocked-down cells were processed further for single cell cloning by limiting dilution method. For generation of EPCR expressing REN cells, REN MPM cells were transfected with pZeoSV plasmid containing human EPCR cDNA (or empty pZeoSV plasmid). Stable transfectant colonies were selected by culturing the transfected cells in RPMI complete medium containing 100 µg/mL of zeocin. Some of the colonies were expanded by limiting dilution, and clones overexpressing EPCR and exhibiting similar TF activity as of control vector transfected or parental REN cells were selected.

MS-1 and M9K MPM cells that constitutively express minimal levels of TF were transfected with pcDNA 3.1 containing TF cDNA (4 µg/6-well plate). After 48 h of transfection, the cells were transferred to complete RPMI medium containing hygromycin B (100 µg/ml; InvivoGen). Colonies of stable transfectants were selected and analyzed for cell surface TF expression levels by measuring their ability to support factor X activation. Stable cell transfectants expressing cell surface TF activity approximately equivalent to that of REN cells were selected and maintained in complete medium containing hygromycin B. To suppress EPCR expression in MS-1 and M9K cells expressing TF, MS-1 and M9K cells stably transfected with TF were re-transfected with EPCR-specific shRNA constructs. The same shRNA constructs were used to knock-down EPCR expression in parental MS-1 and M9K MPM cells. The seed sequences of oligonucleotides used for knock-down of EPCR gene was gene were TGGCCTCCAAAGACTTCATAT (SEQ ID NO:8) and GCAGCAGCTCAATGCCTACAA (SEQ ID NO:9). The procedure for EPCR knock-down was essentially same as that described in the preceding paragraph for knocking-down of TF or PAR1 in REN MPM cells.

Tissue Factor Activity

The procoagulant activity of TF on intact cell surface of wild-type and stable transfectants was measured in a factor X activation assay as described earlier (33). Briefly, confluent cell monolayers were incubated with FVIIa (10 nM) for 5 min at 37° C. in buffer B (buffer A [10 mM Hepes, 0.15 M NaCl, 4 mM KCl, 11 mM glucose, pH 7.5] containing 1 mg/ml BSA and 5 mM $CaCl_2$) followed by addition of factor X (175 nM) to initiate TF-FVIIa activation of factor X. At the end of 5 min activation period, an aliquot was removed and the amount of factor Xa generated was measured in a chromogenic assay using the substrate Chromogenix S-2765 (Aniara, Mason, Ohio).

Measurement of Cytosolic $Ca^{2+}$ Release

Fluorescence microscopy was used for measurement of cytosolic $Ca^{2+}$ release as described earlier (34). MPM cells were seeded in 8-well chambered cover slips (Nunc, Rochester, N.Y.) at a density of 10,000 cells/well. After 24 h, cells were washed and incubated with 4 µM Fluo-4/AM Ester (Molecular Probes, Inc, Eugene, Oreg.) for 1 h in buffer B in a humidified atmosphere of 37° C./5% $CO_2$. The cells were then washed with buffer B, and a chambered cover slip was placed on the stage of an inverted microscope (Axio Observer Z1) encased in an incubation chamber that maintained 37° C./5% $CO_2$. Live images of cell fluorescence were recorded by exciting the Fluo-4 probe with 488 nm light and monitoring 530 nm emission using Carl Zeiss LSM 510 Meta Confocal Laser Scanning system. After 15 sec of image acquisition, PAR1 agonist peptide TFLLRNPNDK; SEQ ID NO:10)) or PAR2 agonist peptide (SLIGRL; (SEQ ID NO:11)) was added to the cells at a final concentration of 50 µM and the recording was continued for an additional 165 sec. Results are represented as change in fluorescence intensity over time.

Cell Proliferation

Cell proliferation assay in MPM cells in the presence or absence of various ligands was performed using Apo-BrdU cell proliferation assay kit from Millipore (Temecula, Calif.) following the manufacturer's instructions. Briefly, MPM cells (7,500 cells/well) were seeded in 96-well plates in RPMI medium containing 10% FBS, and after 24 h the cells were washed once and maintained in serum-free medium (SFM). After 24 h, the cells were washed once with SFM and incubated with SFM or SFM containing FVIIa, APC, thrombin or serum (1%) for 24 h. Twenty µl of BrdU-labeling solution was added to each well 8 h prior to the completion of 24 h incubation with the test compound. The cells were fixed and processed for detection of BrdU incorporation by incubating the cells with an anti-BrdU antibody, followed by peroxidase-conjugated secondary antibody and then the substrate tetramethyl-benzidine with three washings in between each step. The color developed in the assay was measured as absorbance at 450 nm using the absorbance measured at 650 nm as a reference value in a microplate reader (Molecular Devices, Sunnyvale, Calif.).

Orthotopic Murine Model of Thoracic Human MPM

Briefly, cells were detached from the culture dish using non-enzymatic cell dissociation reagent (MP Biomedicals, Solon, Ohio), washed once with phosphate buffered saline (PBS) and resuspended in PBS containing growth factor-reduced Matrigel (BD Biosciences) at 1:4 dilution. One hundred µl of cell suspension containing $10^6$ cells was injected into the pleural cavity of mice using 1 cc syringe with a 25-gauge, ⅝-inch needle. Cells were injected into the thoracic cavity at the interspace between the $8^{th}$ and $9^{th}$ rib instead of injecting perpendicular to the sternum at the left $4^{th}$ and $5^{th}$ interspace as described originally (4). This injection procedure was easier to perform and improved the reproducibility of delivery into the thoracic cavity. Mice were observed on a daily basis for any visible signs of stress and weighed on a weekly basis. Mice were sacrificed between 28 and 30 days following tumor cell implantation, the chest cavities were photographed and tumors were counted. Tumor volumes were calculated as described earlier (4). Tumors greater than 2 mm in size were included in calculations of total tumor volume. All tumors measuring 2 mm or above were excised carefully from the thoracic cavity and weighed as a measure of tumor burden. Tumor and tissue samples were fixed in Excell-Plus fixative (American Mastertech Scientific, Inc.) overnight.

Antibodies and Other Reagents

Preparation of monospecific polyclonal anti-human TF IgG was described earlier (1). Goat anti-human EPCR antibodies, EPCR monoclonal antibodies (JRK1489), and TM monoclonal antibodies (CTM1009) were obtained from Charles Esmon, Oklahoma Medical Research Foundation, Oklahoma City, Okla. Rabbit anti-human TFPI antibodies were provided by George Broze (Washington University Medical Center, St. Louis, Mo.). Monoclonal antibodies for PAR1 (ATAP2), PAR2 (SAM11), and β-actin (C4) were from Santa Cruz Biotechnology (Santa Cruz, Calif.) and GAPDH (MAB374) was from EMD Millipore Chemicals (Billerica, Mass.). Rabbit anti-Ki67 antibody was from Abcam (Cambridge, Mass.) and TUNEL staining kit (Dead-End Colorimetric TUNEL System) was from Promega (Madison, Wis.). PAR1 and PAR2 agonist peptides (TFLL-RNPNDK (SEQ ID NO:10 and SLIGRL (SEQ ID NO:11) were custom synthesized (Biosynthesis, Lewisville, Tex.). Recombinant human FVIIa was obtained from Novo Nor-disk (Maaloev, Denmark) Growth-factor reduced Matrigel was from BD Biosciences (San Jose, Calif.). All other clotting reagents were obtained from either Enzyme Research Laboratories (South Bend, Ind.) or Hematological Technologies (Essex Junction, Vt.).

Histology and Immunohistochemistry

Tissues were processed using graded alcohol and xylene, embedded in paraffin, 5 µm-thin sections were cut and de-paraffinized using standard procedures. Rehydrated sections were processed for hematoxylin-eosin (H&E), elastin or collagen staining. For elastin staining, rehydrated tissue sections were treated overnight with Resorcin-Fuchsin stain and counterstained with Tartrazine. For collagen staining, tissue sections were first stained in picric acid at 65° C. for 30 min followed by trichrome blue for 30 min. For immunostaining, rehydrated sections were processed for antigen retrieval using Dako Antigen Retrieval Solution (Dako North America, Carpinteria, Calif.). Tissue peroxidases were inactivated by treating the tissue sections with 3% $H_2O_2$ for 30 min. Sections were then blocked with Dako antibody diluent solution and stained with control IgG, anti-human TF IgG, anti-human EPCR IgG (5 µg/ml) or anti-Ki67 (1:200 dilution) diluted in blocking buffer. Slides were washed to remove excessive primary antibodies and tissue sections were labeled with biotinylated secondary antibodies followed by streptavidin-HRP using the Biotinylated Link Antibody Kit (Dako). Finally, sections were developed using AEC substrate chromogen and counterstained with hematoxylin followed by mounting with aqueous mounting media. TUNEL staining was performed essentially as described in manufacturer's technical bulletin. Stained sections were viewed under a Nikon eclipse Ti microscope and photographed using Nikon digital sight DS-Fi1 camera and NIS elements BR 3.2 software. All sections were photographed using the same exposure settings. The % of proliferating or apoptotic cells was determined by counting the number of positively stained cells for Ki67 or in TUNEL staining, respectively, among the total number of tumor cells counted in multiple fields.

Statistical Analysis

Nonparametric statistical tests were used to analyze the data. Analysis of variance (ANOVA) was used for multi group comparisons and statistical significance levels were determined by non-parametric Kruskal-Wallis test, followed by Dunn's multiple comparison post test for determination of statistical significance between the two groups within the multi-group. When the data set contained only two groups, statistical significance between the groups was determined by the nonparametric Mann-Whitney test. Differences were considered statistically significant if $P<0.05$. All results were expressed as mean±SEM. Statistical comparisons were done using the GraphPad Prism program (GraphPad software).

EXAMPLE II

Status of TF, EPCR, PAR1 and PAR2 Expression Levels in MPM Cells

The expression levels of TF, EPCR, PAR1 and PAR2 in REN, MS-1 and M9K MPM cells were analyzed by Western blot and functional analyses. TF expression was markedly higher in REN MPM cells compared to MS-1 and M9K MPM cells (FIGS. 1A and B). TF expression was barely detectable in MS-1 and M9K cells. In contrast to TF expression, REN MPM cells express very little EPCR whereas both MS-1 and M9K cells abundantly express EPCR, at levels found in endothelial cells (FIG. 1C). Western blot analysis revealed that all three MPM cell types express PAR1 whereas PAR2 expression was undetectable (FIG. 1D). Consistent with the antigen results, a PAR1 but not PAR2 agonist peptide induced intracellular $Ca^{2+}$ release in REN MPM cells (FIG. 1E). A similar pattern of $Ca^{2+}$ release was observed in MS-1 and M9K MPM cells in response to PAR1 or PAR2 agonist peptides (results not shown).

EXAMPLE III

Figure 2A:
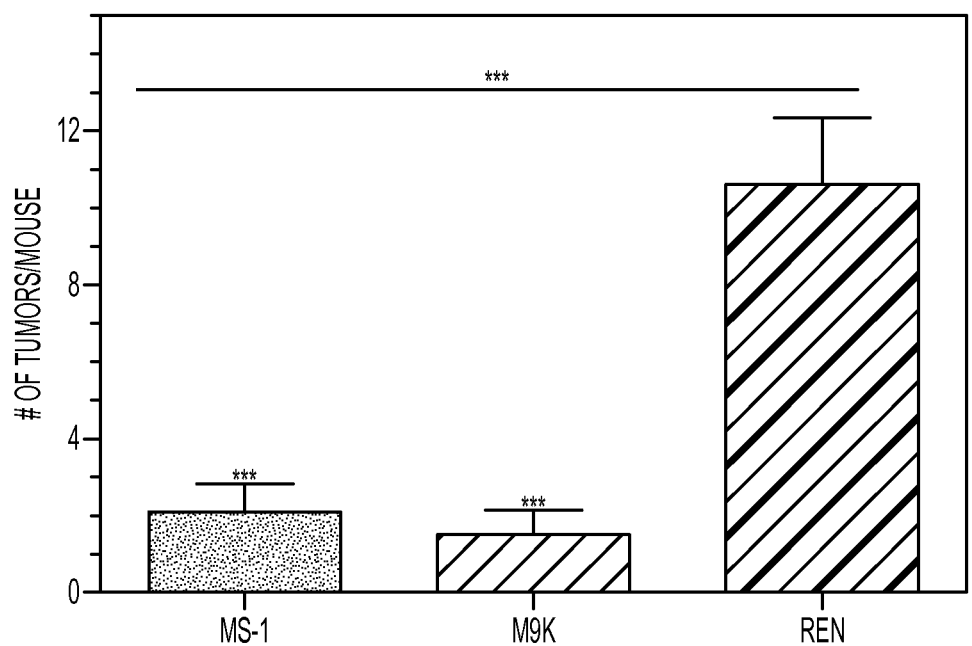
FIG. 2A-2D. REN MPM cells but not MS-1 or M9K MPM cells generate large and invasive intrathoracic tumors.
Figure 2B:
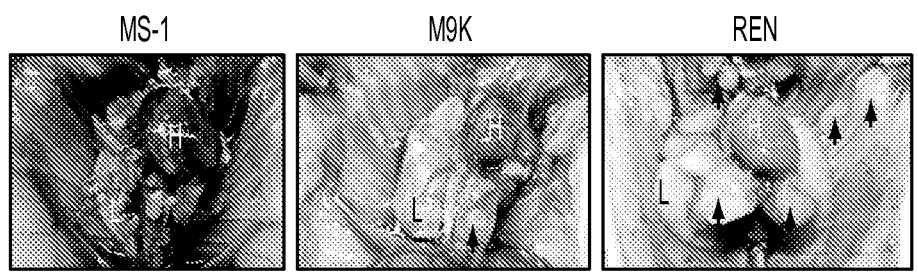
Figure 2C:
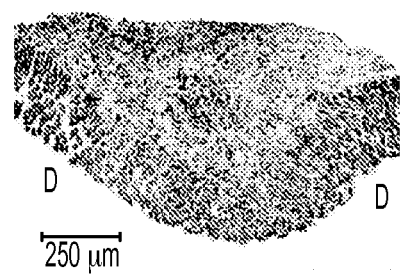
Figure 2D:
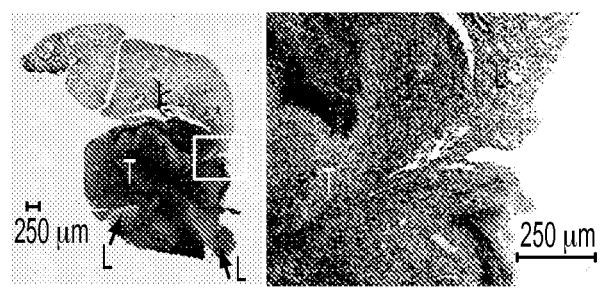

REN MPM Cells Generate Large Invasive Tumors and Knock-Down of TF Reduces Tumorigenicity of REN Cells As reported previously, implantation of REN MPM cells into the thoracic cavity of nude mice resulted in multiple large tumors (>2 mm) within the thoracic cavity (FIG. 2A). The number of tumors in each mouse varied from 6 to 18. Some of the tumors approximated the size of the heart (FIG. 2B). All tumors were limited to the thoracic cavity. These tumors were highly invasive and often penetrated deep into intercostal tissues on which they were attached (FIGS. 2C and 2D). There was no evidence for metastasis as we found no tumors in distant organs such as liver. A variable number of very small tumors (<2 mm) found in the thoracic cavity may reflect dispersed initial seeding of tumor cells than pleural metastases. In contrast to REN, MS-1 and M9K cells in nude mice produced relatively few tumors and some of the mice developed no tumors at all. Most of the tumors that were generated from these cells barely reached the 2 mm size. None of the tumors grew as large as those found in mice injected with REN cells. Further, MS-1 and M9K cell generated tumors were loosely attached to the tissue and remained non-invasive. Intrathoracic lavage of these animals showed small granular white spheroids. No significant differences were observed in cell growth potential among REN, MS-1 and M9K MPM cells in vitro, either under basal conditions or in the presence of serum (results not shown).

Figure 3A:
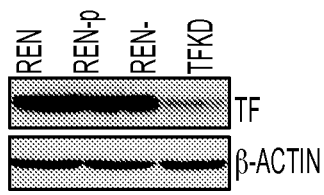
FIG. 3A-3F. Suppression of TF in REN MPM cells attenuates tumor growth. Naïve REN cells were stably transfected with control non-effective scrambled shRNA or TF-specific shRNA in pSilencer vector. The stable transfectants were analyzed for TF expression by western blot analysis (FIG. 3A) or measuring cell surface TF activity (FIG. 3B). Mice were injected with REN, REN-p or REN-TFKD MPM cells, and after 4 weeks mice were sacrificed, and tumor number (FIG. 3C), volume (FIG. 3D) and burden (FIG. 3E) were calculated as described in the methods (Example I). n=10 to 13 mice/group, results from two experiments performed using two independent REN-TFKD stable transfectants, which gave similar results, were pooled). Significance of differences between the groups were determined by Kruskal-Wallis test (P<0.05) with Dunn's post test to compare differences between REN vs. REN-P or REN-TFKD. ns, not significant; P<0.01; ***P<0.001. Values of REN-TFKD were also differed statistically significant manner from values of REN-P (P<0.05).
Figure 3B:
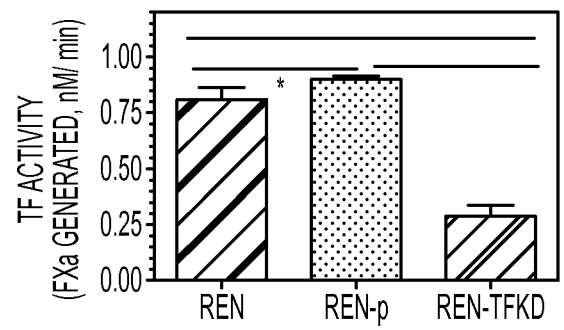
Figure 3C:
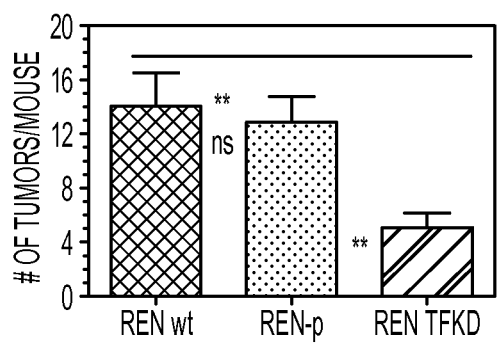
Figure 3D:
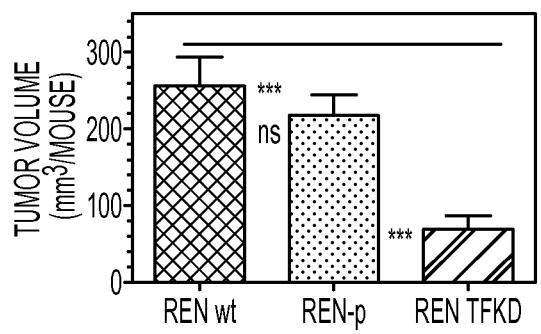
Figure 3E:
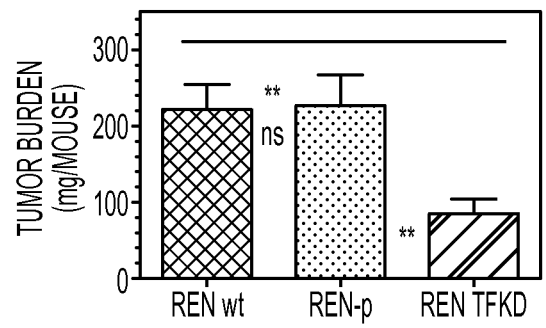
Figure 3F:
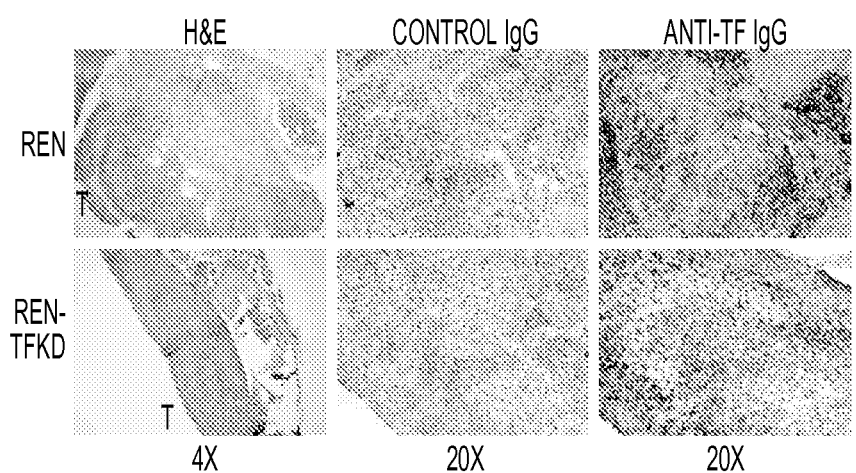
Figure 8:
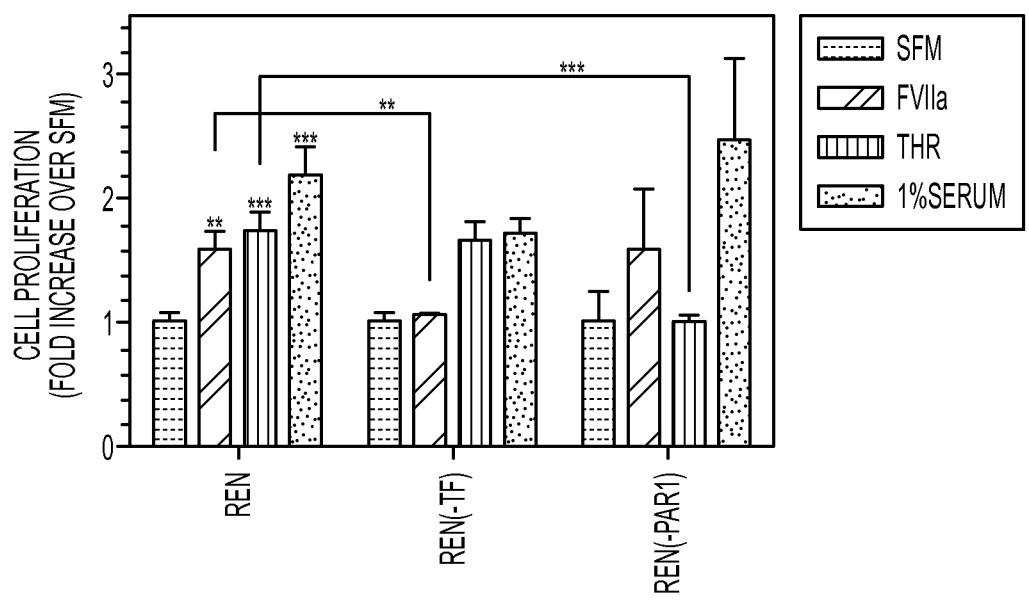
FIG. 8. Effect of FVIIa and thrombin on cell proliferation of wild-type REN, TF- or PAR1-knocked-down REN MPM cells. REN, REN(−TF) or REN(−PAR1) cells were treated with serum-free medium (SFM) or SFM containing FVIIa (10 nM), thrombin (10 nM) or 1% serum for 24 h. Cell proliferation was assayed as described. P<0.01; *P<0.001 (compared to cells grown in SFM or as indicated).

To investigate the role of TF in the aggressiveness exhibited by REN tumors, we knocked-down TF expression in REN cells by stably transfecting with TF-specific shRNA (REN-TFKD). As a control, REN cells were stably transfected with a control non-effective scrambled shRNA in pSilencer vector (REN-p). As shown in FIGS. 3A and 3B, TF antigen expression and cell surface TF activity was reduced by about 70% in REN-TFKD cells compared to that measured in naive REN or REN-p cells (FIGS. 3A and 3B). Next, naïve REN cells, REN-p or REN-TFKD cells were injected intrapleurally into nude mice and tumor growth and burden were evaluated 4 weeks after tumor cell implantation. Mice injected with naïve REN and REN-p cells developed a similar number of large tumors (FIG. 3C) and no significant differences were found between them in their tumor growth or burden (FIG. 3D and FIG. 3E). In contrast, mice injected with REN-TFKD cells developed fewer numbers of large tumors (FIG. 3C). Although a few of the tumors in mice injected with REN-TFKD grew as large as those found in mice injected with naïve REN or REN-p cells, most of the tumors were smaller. The total tumor volume and burden was significantly lower in mice injected with REN-TFKD cells in relation to mice injected with naïve REN or REN-p cells (FIGS. 3D and 3E). In contrast to tumors originating from naïve REN and REN-p cells, tumors that originated from REN-TFKD were less invasive (results not shown) Immunohistochemical analysis of tissue sections using anti-TF antibodies showed abundant expression of TF in tumors that developed in mice injected with naïve REN or REN-p cells. In contrast, little expression of TF was found in tumors from mice injected with REN-TFKD (FIG. 3F). In vitro cell proliferation studies showed that FVIIa increased the cell proliferation of REN cells modestly but consistently and TF knock-down abrogated responsiveness to FVIIa (FIG. 8).

Figure 4A:
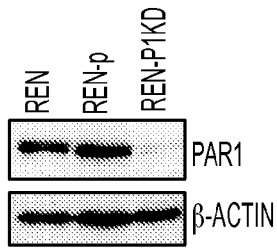
FIG. 4A-4F. PAR1 knock-down in REN-MPM cells reduces tumor growth and burden of REN tumors. REN cells were stably transfected with control non-effective scrambled shRNA or PAR1-specific shRNA. The stable transfectants were analyzed for PAR1 expression by western blot analysis (FIG. 4A) or measuring intracellular $Ca^{2+}$ release in response to PAR1 peptide agonist (FIGS. 4B and 4C). Stable transfectants of REN cells expressing control shRNA (REN-p) or PAR1-specific shRNA (REN-P1KD) were injected intrathoracically into nude mice ($10^6$ cells/mouse). After 4 weeks, mice were sacrificed, and tumor volume (FIG. 4D) and burden (FIG. 4E) were calculated as described in Example I. n=7 to 9 mice/group, results from two independent experiments performed with a single REN-P1KD clone was combined). Statistical significance between the two groups was determined by Mann-Whitney test; ***P<0.001.
Figure 4B:
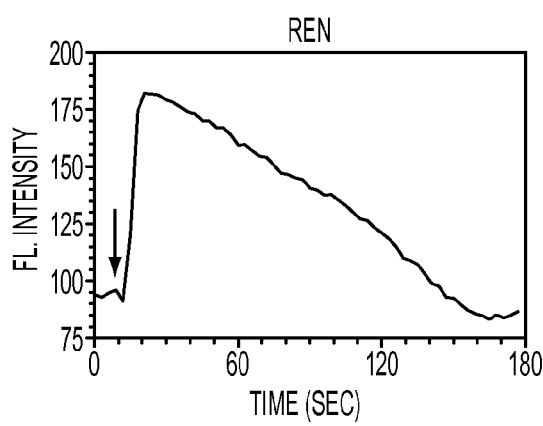
Figure 4C:
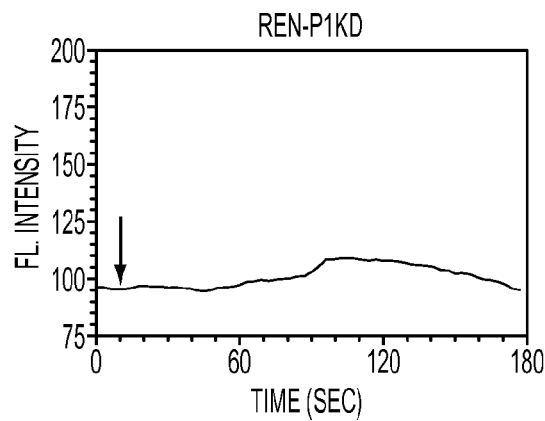
Figure 4D:
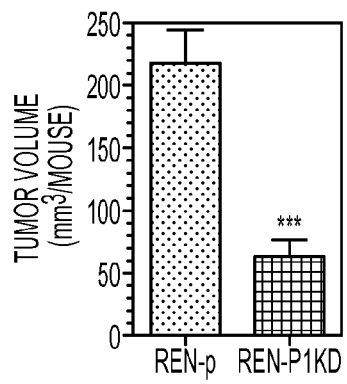
Figure 4E:
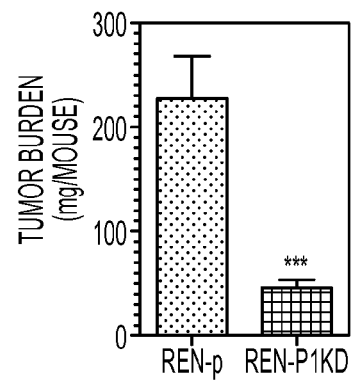
Figure 4F:
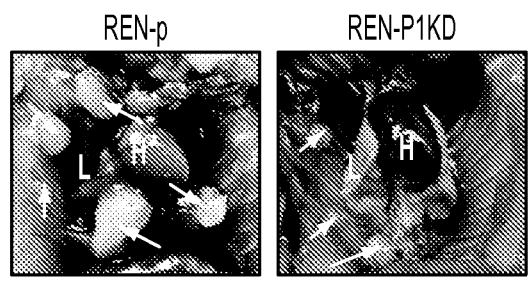

Earlier studies showed that tumor growth in breast cancer was dependent on TF-FVIIa-PAR2 cell signaling, independent of PAR1 (17, 21). Since REN MPM cells express PAR1 and not PAR2, we considered the possibility that TF promotes tumor growth of MPM through a PAR1-dependent mechanism. To examine this possibility, PAR1 expression in REN MPM cells was knocked-down by PAR1-specific shRNA (REN-P1KD). PAR1 knock-down reduced the PAR1 expression by more than 80% (FIGS. 4A, 4B and 4C). Knocking-down PAR1 in REN MPM cells resulted in more than 50% reduction in the number of tumors formed in the thoracic cavity of nude mice compared to nude mice injected with naïve REN and REN-p cells (REN, 16.0±3.5; REN-p, 12.9±1.8; REN-P1KD, 6.3±0.8). As shown in FIGS. 4D, 4E and 4F, inhibition of PAR1 expression in REN cells markedly attenuated tumor growth and burden. In addition, PAR1 knock-down also eliminated the invasiveness of REN tumors. In vitro cell proliferation studies showed that PAR1 knock-down diminished a modest increase of thrombin-induced cell proliferation (FIG. 8).

EXAMPLE IV

Figure 5A:
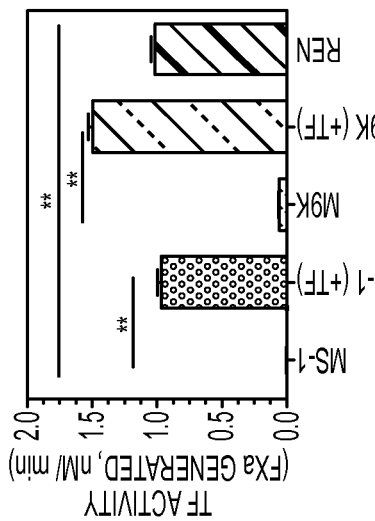
FIG. 5A-5F. Overexpression of TF does not increase the tumorigenicity of non-aggressive MS-1 or M9K MPM cells. MS-1 and M9K cells were transfected with tissue factor (TF) expression vector and stable cell transfectants expressing TF were selected. TF expression was analyzed by Western blot analysis (FIG. 5A) or measuring cell surface TF coagulant activity in factor X activation assay (FIG. 5B).
Figure 5B:
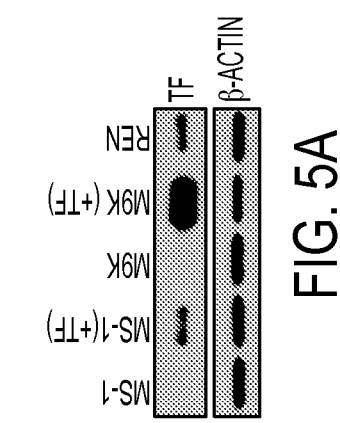
Figure 5C:
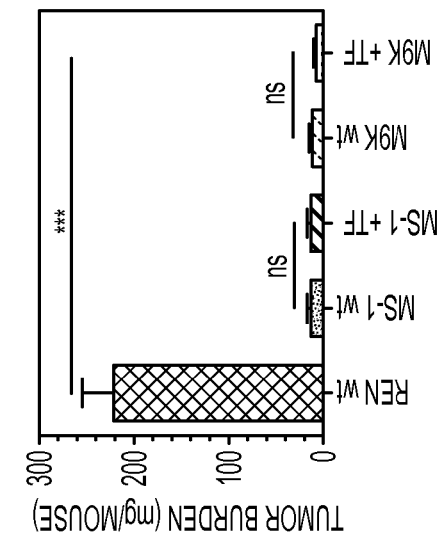
Figure 5D:
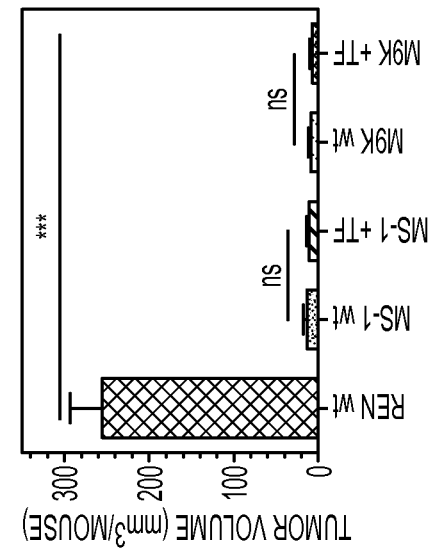
Figure 5E:
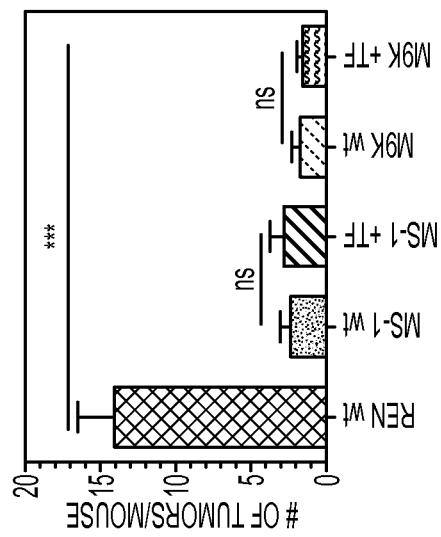
Figure 5F:
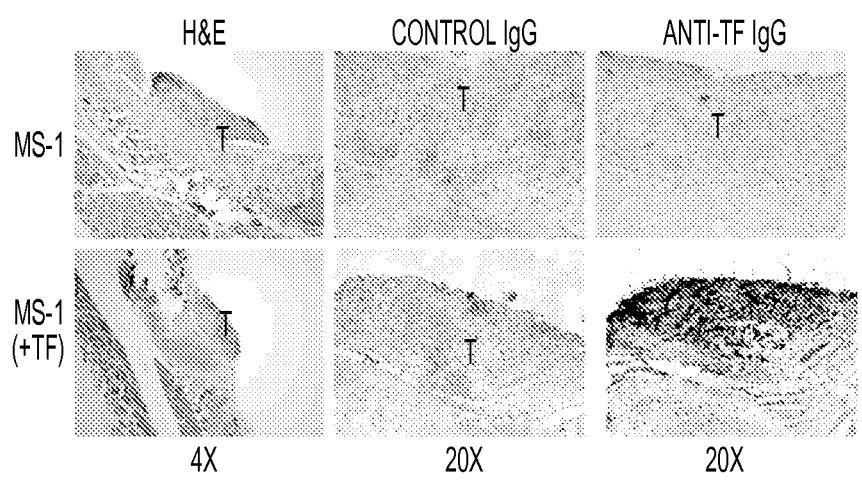

Overexpression of TF in Less Aggressive MS-1 and M9K MPM Cells does not Increase the Tumorigenicity of these Cell Types To determine whether differences in TF expression alone are responsible for marked differences in the tumor growth of aggressive REN MPM cells and less aggressive MS-1 and M9K cells, MS-1 and M9K cells were stably transfected to express human TF. MS-1 and M9K transfectants expressing similar levels of cell surface TF functional activity as that found in REN MPM cells (FIG. 5B) were selected for in vivo studies. Surprisingly, overexpression of TF in either MS-1 or M9K cells failed to alter their tumorigenicity. The number of tumors formed in the pleural cavity of nude mice injected with MS-1(+TF) or M9K(+TF) cells was comparable to those formed in the mice injected with naïve MS-1 and M9K cells, and these were markedly less than the number of tumors in nude mice injected with naïve REN cells (FIG. 5C). The tumors formed in nude mice injected with naive or TF over expressing MS-1 or M9K cells were small and barely reached the 2 mm size-threshold to be included in the total tumor count. Further, these small tumors were loosely adhered to the pleura in contrast to the tumors formed in mice injected with REN cells which were firmly attached and were invasive. No significant differences were observed in the tumor volume (FIG. 5D) or tumor burden (FIG. 5E) among mice injected with naïve and TF over expressing MS-1 or M9K cells, which were significantly lower (P<0.001) than that measured in mice injected with naïve REN cells. Immunohistochemical analysis of tumor sections revealed that MS-1 (FIG. 5F) and M9K cells (results not shown) stably transfected with TF continued to express TF in the tumor environment in vivo. Analysis of lysates of tumors excised from mice by Western blot analysis and TF functional activity assays confirmed the presence of TF in small tumors generated by MS-1(+TF) and M9K (+TF) cells (results shown). These results eliminate the possibility that loss of TF expression in tumor cells in vivo could be responsible for the inability of TF to promote tumor growth in these cell types.

EXAMPLE V

EPCR Regulates TF-Driven Tumor Growth of MPM

Figure 6A:
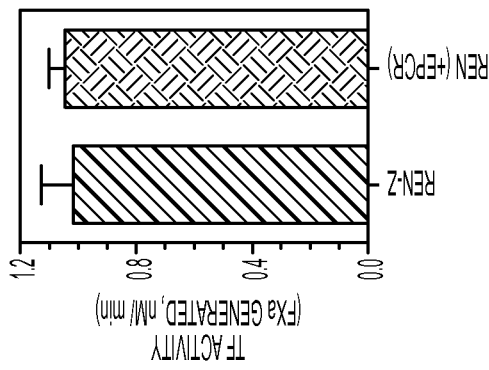
FIG. 6A-6F. EPCR expression in tumor cells reduced tumorigenicity of aggressive REN MPM cells. REN MPM cells were stably transfected with pZeoSV or pZeoSV+EPCR expression vector and analyzed for EPCR expression by western blot (FIG. 6A) and cell surface TF activity (FIG. 6B). REN cells expressing the control vector (REN-Z) or EPCR expression vector (REN (+EPCR)) were injected intrathoracically into nude mice ($10^6$ cells/mouse). After 30 days, mice were sacrificed, and tumor number (FIG. 6C), volume (FIG. 6D) and burden (FIG. 6E) were measured. Results were combined from two independent experiments performed with three independent EPCR overexpressing clones, which gave very similar results; n=11 to 17 mice/group). Statistical significance of differences between groups was determined by the Mann-Whitney test; ***P<0.0001 compared to REN-Z.
Figure 6B:
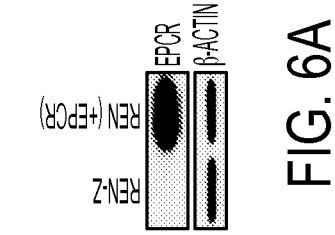
Figure 6C:
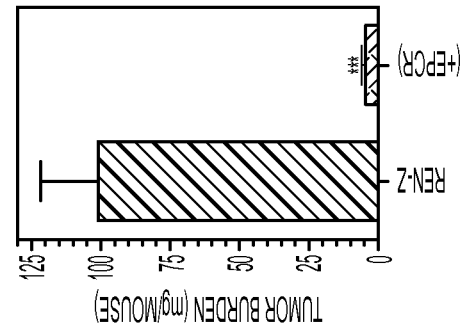
Figure 6D:
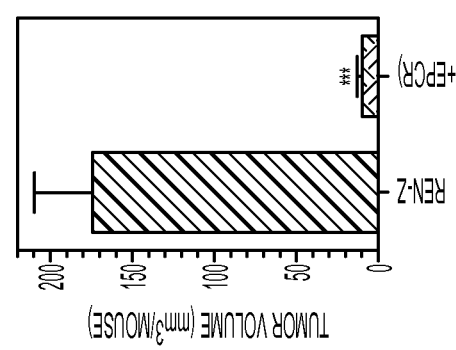
Figure 6E:
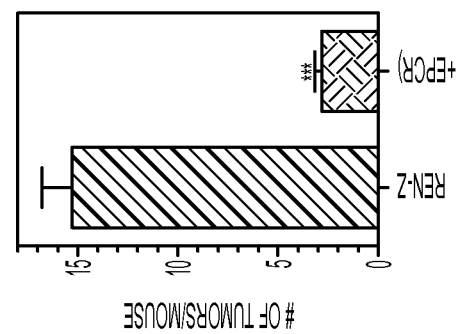
Figure 6F:
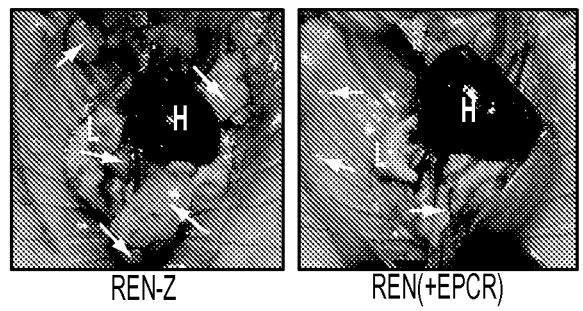
Figure 9A:
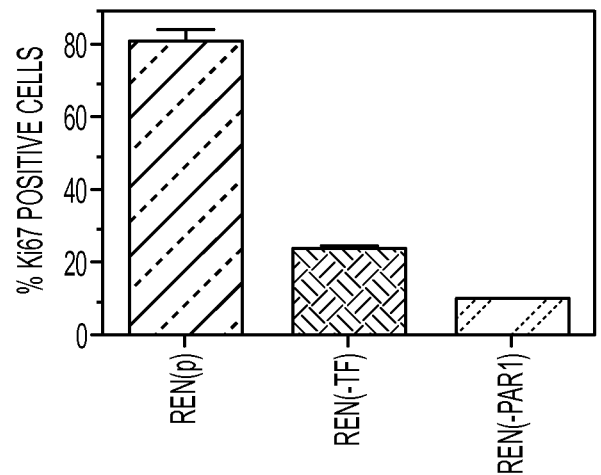
FIG. 9A-9B. TF- or PAR1 knock-down in REN MPM cells suppresses in vivo tumor cell proliferation. Tissue sections of tumors derived from mice injected with REN(p), REN(−TF) or REN(−PAR1) MPM cells were immunostained for the presence of nuclear proliferation antigen Ki67. The percentage of proliferating cells was determined by counting the number of tumor cells stained positively with Ki67 antibodies in the nucleus and the total number of tumor cells counted in multiple fields (the total number of tumor cell counted was set to 100%). The images represent a small portion of immunostained tumor tissue section.
Figure 9B:
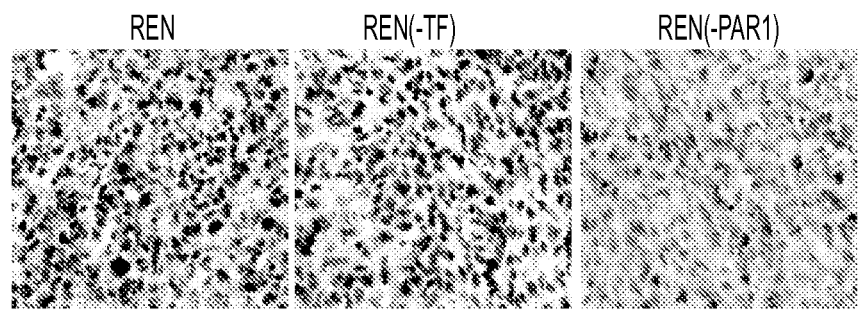
Figure 10A:
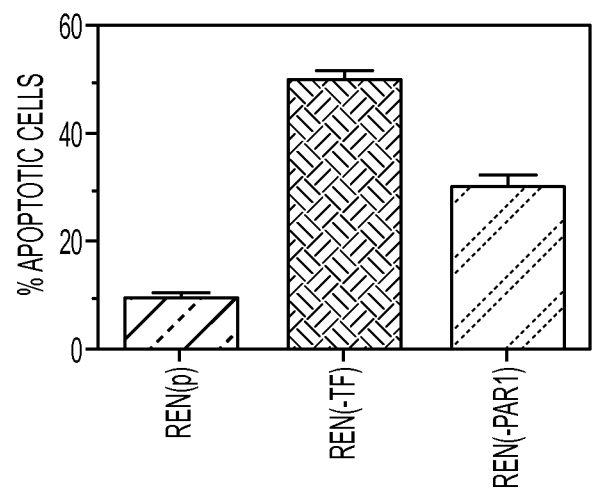
FIG. 10A-10B. TF- or PAR1 knock-down in REN MPM cells increases tumor cell apoptosis in vivo. Tissue sections of tumors derived from mice injected with REN(p), REN(−TF) or REN(−PAR1) MPM cells were stained for TUNEL. The percentage of apoptotic cells was determined by counting the number of tumor cells stained positive for TUNEL staining among the total number of tumor cells counted in multiple fields (the total number of tumor cells counted was set to 100%). The images represent a portion of immunostained tumor tissue section.
Figure 10B:
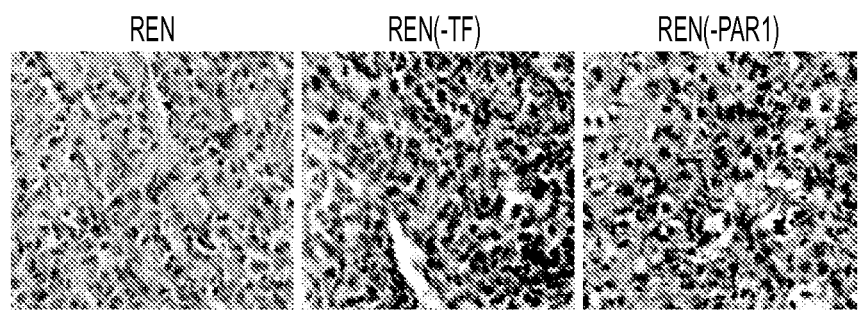
Figure 11:
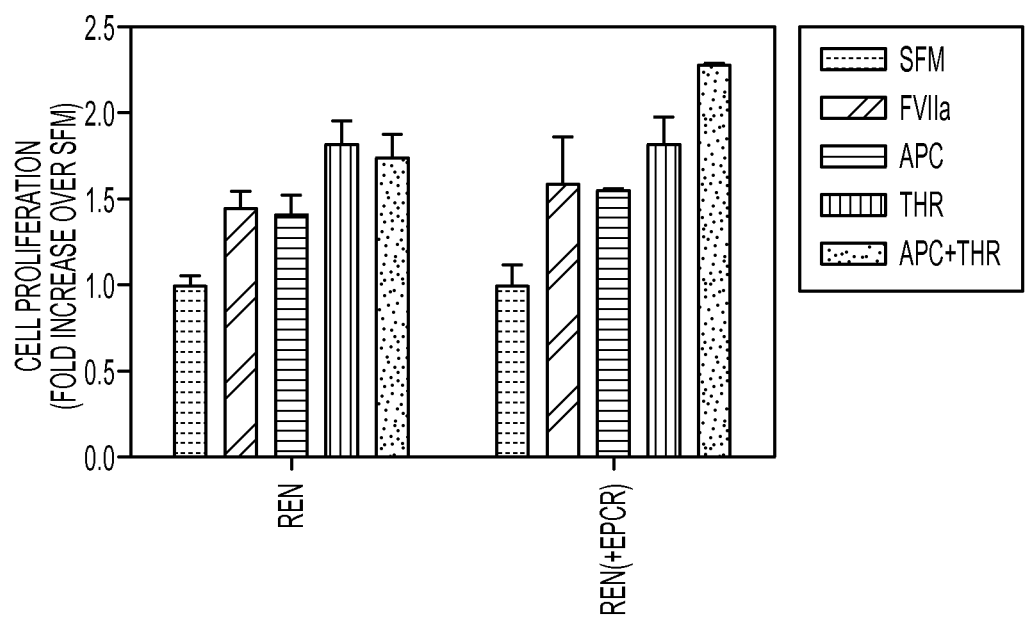
FIG. 11. Overexpression of EPCR did not alter in vitro growth potential of REN MPM cells. REN cells or REN cells stably transfected with EPCR expression REN(+EPCR) were incubated with SFM or SFM containing FVIIa (10 nM activated protein C (APC, 20 nM thrombin (10 nM APC (20 nM)+thrombin (10 nM) or 1% serum for 24 h. Cell proliferation was assayed by BrdU incorporation. Differences in cell proliferation between REN and REN(+EPCR) treated with various ligands was not statistically significant.
Figure 12A:
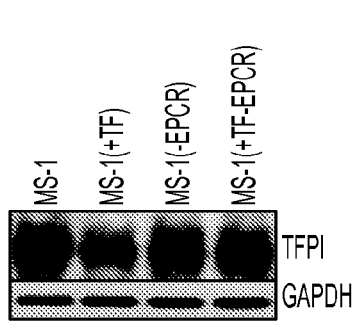
FIG. 12A-12B. Tissue factor pathway inhibitor (TFPI) and thrombomodulin (TM) protein levels in parental MS-1 (A) and M9K (B) MPM cells and their variants was analyzed by western blot analysis.
Figure 12B:
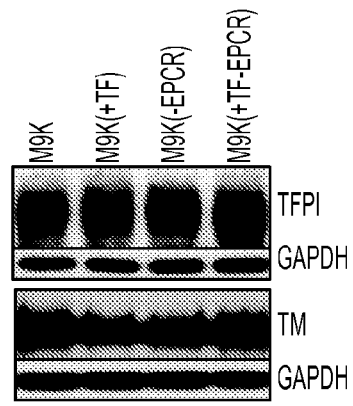
Figure 13A:
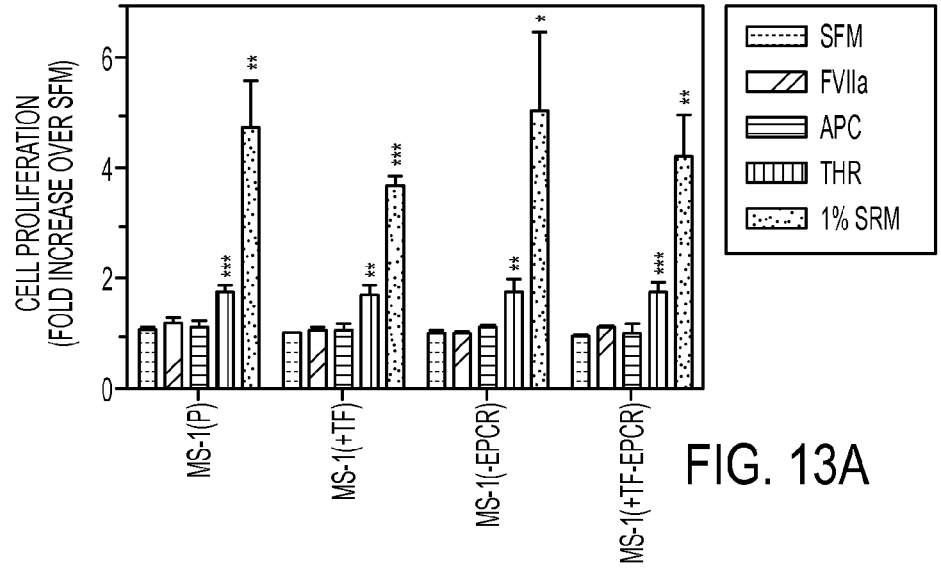
FIG. 13A-13B. EPCR knock-down did not alter cell proliferation of MS-1 or M9K MPM cells in vitro. MS-1 (FIG. 13A) or M9K (FIG. 13B) MPM cells stably transfected with a control plasmid, TF, EPCR shRNA, or TF and EPCR shRNA plasmids were incubated with SFM or SFM containing FVIIa (10 nM APC (20 nM thrombin (10 nM), or 1% serum for 24 h. Cell proliferation pattern of EPCR expressing MS-1/M9K MPM cells and corresponding EPCR knocked-down MS-1/M9K MPM cells upon treatment with various ligands is not statistically significant. *P<0.05; P<0.01; *P<0.001 compared to cells grown in SFM.
Figure 13B:
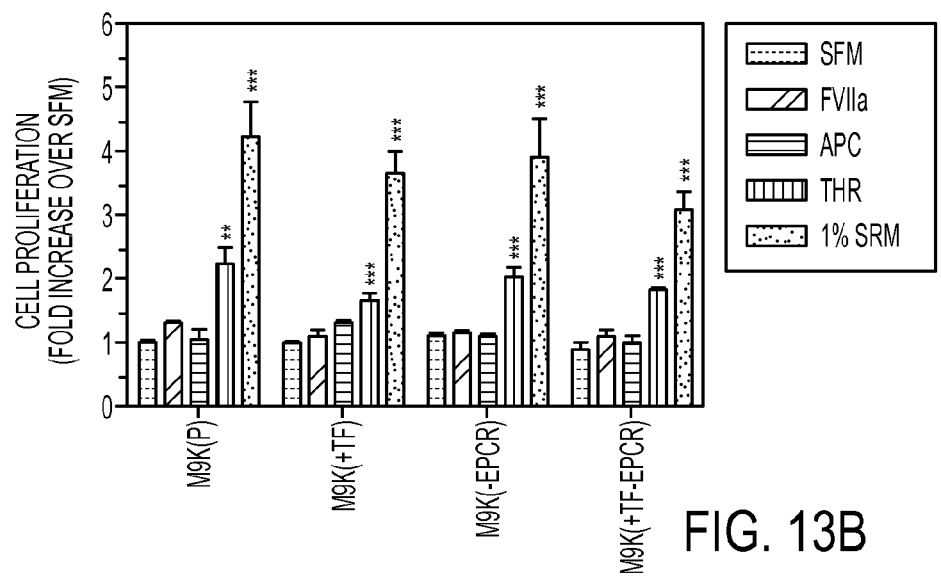

As described above, there is a notable difference between REN and MS-1 or M9K MPM cells in the expression of EPCR, i.e., REN cells do not express EPCR whereas MS-1 and M9K cells express abundant EPCR (FIG. 1C). The present inventors postulated that absence of EPCR in REN MPM cells is responsible for their aggressive tumorigenicity and therefore investigated the potential effect of tumor cell associated EPCR on suppression of MPM tumor growth. REN MPM cells were stably transfected to express EPCR (FIG. 6A). EPCR stable transfectants expressing levels of TF activity similar to that of naïve REN cells or REN cells stably transfected with control vector were selected for intrapleural injection (FIG. 6B). Introduction of EPCR expression to REN cells markedly reduced the number of tumors formed in the thoracic cavity (FIG. 6C), and the few tumors that were formed remained very small (FIG. 6F). Thus, the total tumor volume and burden in mice injected with REN(+EPCR) cells was markedly lower than that was observed in mice injected with control REN-Z cells (FIGS. 6D and 6E). In vitro studies showed no measurable differences in cell proliferation between REN and REN(+EPCR) in the presence or absence of FVIIa, APC or thrombin (FIG. 9).

Figure 7F:
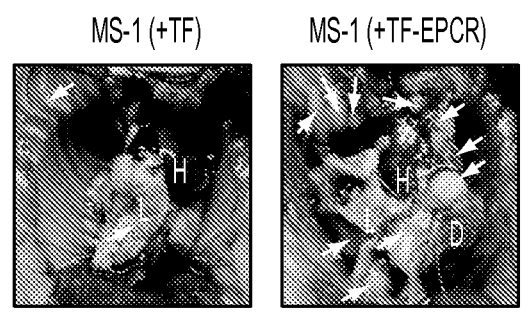
Figure 7G:
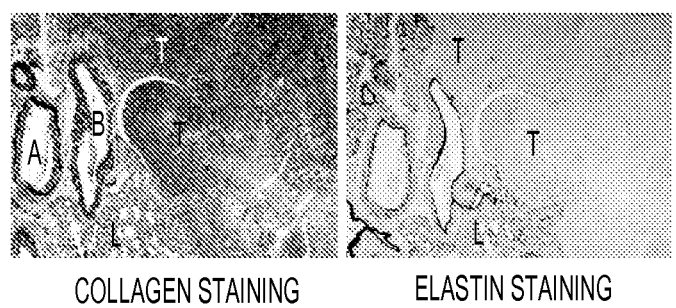

Consistent with the inventors' conception that EPCR plays the critical role in suppressing tumor growth in MPM, knock-down of EPCR expression in TF overexpressing MS-1 and M9K cells dramatically increased the tumorigenicity of these non-aggressive MPM cells (FIG. 7). Mice injected with EPCR-knock-down of MS-1(+TF) and M9K (+TF) MPM cells developed enormous tumor burden. These MPM cell types formed not only large nodular tumors but they grew on lung pleura and diaphragm forming large coalescing tumors that tightly attached the bottom of lungs to diaphragm and esophagus, creating a large thick mass containing tumor cells, organs and the extracellular matrix. In addition, small tumors on pericardial membrane and parietal pleura are clearly visible. Invasion of tumor cells into the intercostal space and along the ribs is also visible in all the mice injected with EPCR-knock-down MPM cells. The thoracic cavities of these mice were filled with bloody fluid (hemothorax). Finally, some of the mice injected with EPCR knock-down of MS-1(+TF) or M9K(+TF) cells lost about 25% body weight in the last one week. These results clearly illustrates critical role of EPCR in suppressing tumorigenicity of MPM cells.

EXAMPLE VI

EPCR Expression Sensitizes MPM Cells to Killing by IFNγ and TNFα

Introduction of EPCR expression to MPM cells that lack EPCR make them highly susceptible to cell death upon treatment with tumor necrosis factor-α (TNFα) and interferon- (IFNγ). REN cells transfected with control vector (REN) or EPCR (REN(+EPCR)) were treated with a control vehicle or IFNγ+TNFα (20+10 ng/ml) for 72 hours. Apoptosis was measured by TUNEL/flow cytometry analysis. Cells gated in the right quadrant represent apoptotic cells.

Figure 14:
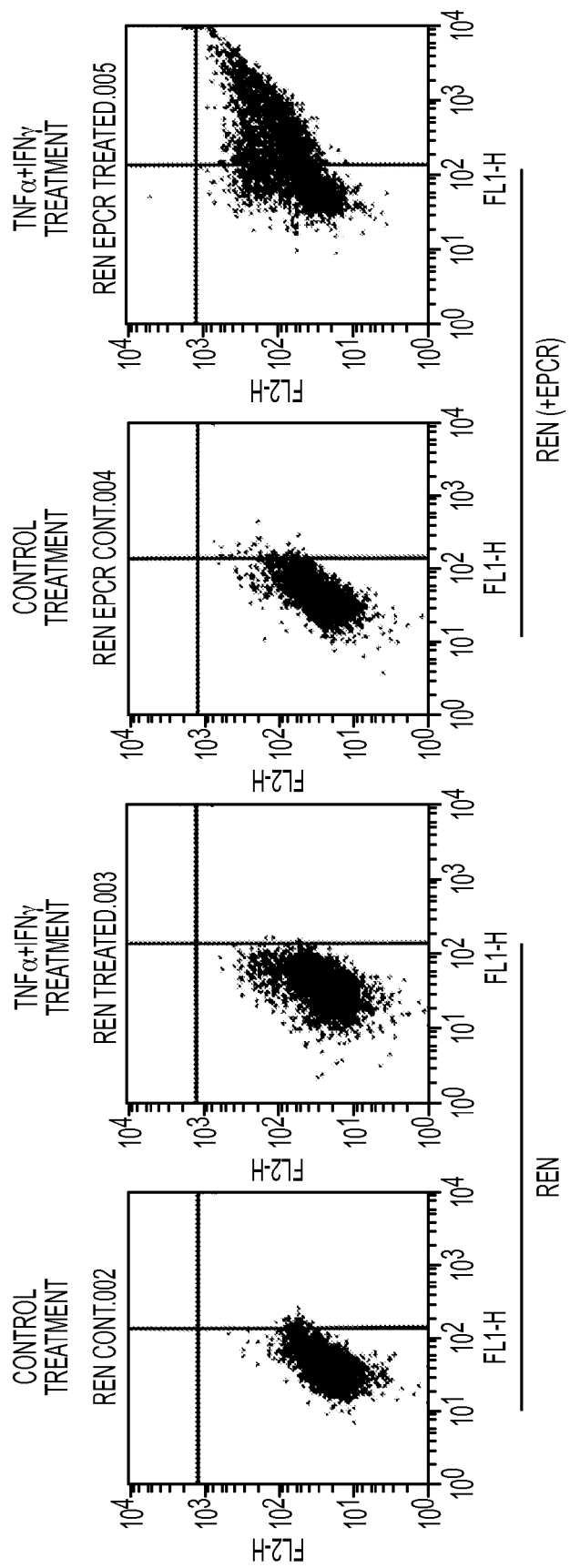
FIG. 14. Increased IFNγ/TNFα-induced apoptosis of tumor cells expressing EPCR. REN cells transfected with control vector (REN) or EPCR (REN(+EPCR)) were treated with a control vehicle or IFNγ (20 ng/ml)+TNFα (10 ng/ml) for 72 hours. Apoptosis was measured by TUNEL/flow cytometry analysis. Cells gated in the right quadrant represent apoptotic cells.

Results are shown in FIG. 14 demonstrate that EPCR expression sensitized the cells, rendering them highly susceptible to cell death upon treatment with tumor necrosis factor-α (TNFα) and interferon- (IFNγ).

Therefore, according to the present invention, inducing or increasing EPCR expression as described above may be used to treat MPM in a subject, in which case, endogenous levels of IFNγ or TNFα may contribute to the anti-cancer effect. However, in addition IFNγ may be administered alone, and allowed to interact with endogenous TNFα, in mimicking this effect observed in vitro. Due to its toxicity, TNFα would preferably not be administered, or would be administered in extremely low doses based on the current knowledge in the art, to stimulate MPM cell death and treatment effects.

EXAMPLE VII

EPCR Gene Therapy of Established MPM

Nude mice were injected with (human) REN MPM cells ($10^6$ cells/mice) intrathoracically. After establishment of mesothelioma for 10 days, on day 11, the mice were divided randomly into the following three groups, consisting of 5 mice per group:
1. No Treatment (No Tr)
2. Intrathoracic injection adenoviral particles encoding green fluorescent protein (GFP) as a control (Con AdV) ($10^9$ virions/mouse);
(3) Intrathoracic injection adenoviral particles encoding EPCR (EPCR AdV) ($10^9$ virions/mouse).

Figure 15:
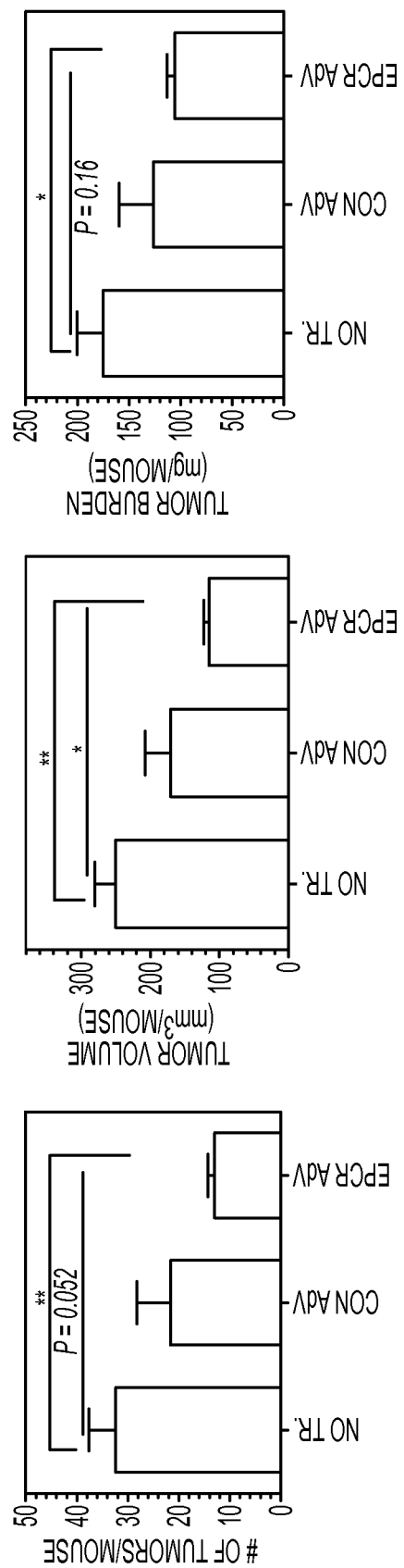
FIG. 15. Effect of EPCR gene therapy on tumor growth of established MPM. Nude mice were injected with REN MPM cells ($10^6$ cells/mouse) intrathoracically. On day 11, mice split into three and either not treated (No Tr.) or injected intrathoracically with adenoviral particles encoding GFP as a control (Con AdV) or encoding EPCR (EPCR AdV) ($10^9$ particles/mouse). The adenovirus injections were repeated at 3 day intervals. Mice were killed at Day 28, and tumors in thoracic cavity were enumerated, excised and measured and weighed to determine tumor volume and burden. Statistical significance of differences were determined by one-way ANOVA using the non-parametric t-test to calculate significance of differences between the two groups. (*, p<0.05; **, p<0.01).

The adenoviral injections were repeated at 3 day intervals. Mice were killed at Day 28, and tumor in their thoracic cavity were enumerated. Additionally tumors were excised from the thoracic cavity, their dimensions measured for tumor volume and they were weighed to calculate tumor burden. One-way ANOVA analysis was used to determine statistical significance of differences between the three groups. Non-parametric t-test was used to calculate statistical significance between the two groups The results, shown in FIG. 15, demonstrate that EPCR treatment resulted in statistically significant reduction in number of tumors per mouse, tumor volume and tumor burden when compared to both control groups as the indicated level of statistical significance. Therefore this form of therapy is effective in treating existing MPM.

REFERENCES CITED BY NUMBER ABOVE (1) Trousseau A. Phlegmasia alba dolens. Clinique medicale de l'Hotel-Dieu de Paris. The New Sydenham Society 1865; 3:654-712.
(2) Sack G H, Levin J, Bell W R. Trousseau's syndrome and other manifestations of chronic disseminated coagulopathy in patients with neoplasms: clinical, pathophysiologic, and therapeutic features. Medicine 1977; 56:1-37.
(3) Rickles F R, Edwards R L. Activation of Blood Coagulation in Cancer: Trousseau's Syndrome revisited. Blood 1983; 62:14-31.

(4) Palumbo J S. Mechanisms linking tumor cell-associated procoagulant function to tumor dissemination. Semin Thromb Hemost 2008; 34:154-60.
(5) Ruf W, Mueller B M. Tissue factor in cancer angiogenesis and metastasis. Curr Opin Hematol 1996; 3:379-84.
(6) Nierodzik M L, Karpatkin S. Thrombin induces tumor growth, metastasis, and angiogenesis: Evidence for a thrombin-regulated dormant tumor phenotype. Cancer Cell 2006; 10:355-62.
(7) Ruf W, Yokota N, Schaffner F. Tissue factor in cancer progression and angiogenesis. Thromb Res 2010; 125 Suppl 2:S36-S38.
(8) Kasthuri R S, Taubman M B, Madman N Role of tissue factor in cancer. J Clin Oncol 2009; 27:4834-8.
(9) van den Berg Y W, Osanto S, Reitsma P H, Versteeg H H. The relationship between tissue factor and cancer progression: insights from bench and bedside. Blood 2012; 119:924-32.
(10) Ruf W, Mueller B M. Thrombin generation and the pathogenesis of cancer. Semin Thromb Hemost 2006; 32 Suppl 1:61-8.
(11) Fischer E G, Ruf W, Mueller B M. Tissue factor-initiated thrombin generation activates the signalling thrombin receptor on malignant melanoma cells. Cancer Research 1995; 55:1629-32.
(12) Palumbo J S, Talmage K E, Massari J V, La Jeunesse C M, Flick M J, Kombrinck K W, et al. Tumor cell-associated tissue factor and circulating hemostatic factors cooperate to increase metastatic potential through natural killer cell-dependent and -independent mechanisms. Blood 2007; 110:133-41.
(13) Camerer E. Protease signaling in tumor progression. Thromb Res 2007; 120 Suppl 2:S75-S81.
(14) Van Sluis G L, Buller H R, Spek C A. The role of activated protein C in cancer progression. Thromb Res 2010; 125 Suppl 2:S138-S142.
(15) Bezuhly M, Cullen R, Esmon C T, Morris S F, West K A, Johnston B, et al. Role of activated protein C and its receptor in inhibition of tumor metastasis. Blood 2009; 113:3371-4.
(16) Horowitz N A, Blevins E A, Miller W M, Perry A R, Talmage K E, Mullins E S, et al. Thrombomodulin is a determinant of metastasis through a mechanism linked to the thrombin binding domain but not the lectin-like domain Blood 2011; 118:2889-95.
(17) Versteeg H H, Schaffner F, Kerver M, Petersen H H, Ahamed J, Felding-habermann B, et al. Inhibition of tissue factor signaling suppresses tumor growth. Blood 2008; 111:190-9.
(18) Yu J L, May L, Lhotak V, Shahrzad S, Shirasawa S, Weitz J I, et al. Oncogenic events regulate tissue factor expression in colorectal cancer cells: implications for tumor progression and angiogenesis. Blood 2005; 105:1734-41.
(19) Hembrough T A, Swartz G M, Papathanassiu A, Vlasuk G, Rote W E, Green S J, et al. Tissue factor/factor VIIa inhibitors block angiogenesis and tumor growth through a nonhemostatic mechanism. Cancer Res 2003; 36:2997-3000.
(20) Amirkhosravi A, Meyer T, Amaya M, Davila M, Mousa S A, Robson T, et al. The role of tissue factor pathway inhibitor in tumor growth and metastasis. Semin Thromb Hemost 2007; 33:643-52.
(21) Versteeg H H, Schaffner F, Kerver M, Ellies L G, Andrade-Gordon P, Mueller B M, et al. Protease-activated receptor (PAR) 2, but not PAR1, signaling promotes the development of mammary adenocarcinoma in polyoma middle T mice. Cancer Res 2008; 68:7219-27.
(22) Williams L, Tucker T A, Koenig K, Allen T, Rao L V, Pendurthi U, et al. Tissue Factor Pathway Inhibitor Attenuates the Progression of Malignant Pleural Mesothelioma in Nude Mice. Am J Respir Cell Mol Biol 2011.
(23) Ghosh S, Pendurthi U R, Steinoe A, Esmon C T, Rao L V. Endothelial cell protein C receptor acts as a cellular receptor for factor VIIa on endothelium. J Biol Chem 2007; 282:11849-57.
(24) Preston R J, Ajzner E, Razzari C, Karageorgi S, Dua S, Dahlback B, et al. Multifunctional specificity of the protein C/activated protein C Gla domain J Biol Chem 2006; 281:28850-7.
(25) Lopez-Sagaseta J, Montes R, Puy C, Diez N, Fukudome K, Hermida J. Binding of factor VIIa to the endothelial cell protein C receptor reduces its coagulant activity. J Thromb Haemost 2007; 5:1817-24.
(26) Sen P, Gopalakrishan R, Kothari H, Keshava S, Clark C, Esmon C T, et al. Factor VIIa bound to endothelial cell protein C receptor activates protease activated receptor-1 and mediates cell signaling and barrier protection. Blood 2011; 117:3199-208.
(27) Disse J, Petersen H H, Larsen K S, Persson E, Esmon N, Esmon C T, et al. The endothelial protein c receptor supports tissue factor ternary coagulation initiation complex signaling through protease-activated receptors. J Biol Chem 2011; 286:5756-67.
(28) Beaulieu L M, Church F C. Activated protein C promotes breast cancer cell migration through interactions with EPCR and PAR-1. Exp Cell Res 2007; 313: 677-87.
(29) Gramling M W, Beaulieu L M, Church F C. Activated protein C enhances cell motility of endothelial cells and MDA-MB-231 breast cancer cells by intracellular signal transduction. Exp Cell Res 2010; 316:314-28.
(30) Van Sluis G L, Niers T M, Esmon C T, Tigchelaar W, Richel D J, Buller H R, et al. Endogenous activated protein C limits cancer cell extravasation through sphingosine-1-phosphate receptor 1-mediated vascular endothelial barrier enhancement. Blood 2009; 114:1968-73.
(31) Anton I, Molina E, Luis-Ravelo D, Zandueta C, Valencia K, Ormazabal C, et al. Receptor of Activated Protein C Promotes Metastasis and Correlates with Clinical Outcome in Lung Adenocarcinoma. Am J Respir Crit Care Med 2012.
(32) Rao L V M. Characterization of anti-tissue factor antibody and its use in immunoaffinity purification of human tissue factor. Thromb Res 1988; 51:373-84.
(33) Pendurthi U R, Williams if, Rao L V M. Acidic and basic fibroblast growth factors suppress transcriptional activation of tissue factor and other inflammatory genes in endothelial cells.
Arterioscler Thromb Vasc Biol 1997; 17:940-6.
(34) Mandal S K, Pendurthi U R, Rao L V. Tissue factor trafficking in fibroblasts: involvement of protease-activated receptor-mediated cell signaling. Blood 2007; 110: 161-70.
(35) Tucker T A, Dean C, Komissarov A A, Koenig K, Mazar A P, Pendurthi U, et al. The urokinase receptor supports tumorigenesis of human malignant pleural mesothelioma cells. Am J Respir Cell Mol Biol 2010; 42:685-96.
(36) Riewald M, Ruf W. Mechanistic coupling of protease signaling and initiation of coagulation by tissue factor. Proc Natl Acad Sci USA 2001; 98:7742-7.

(37) Camerer E, Huang W, Coughlin S R. Tissue factor- and factor X-dependent activation of protease-activated receptor-2 by factor VIIa. Proc Natl Acad Sci USA 2000; 97:5255-60.
(38) Hjortoe G M, Petersen L C, Albrektsen T, Sorensen B B, Norby P L, Mandal S K, et al. Tissue factor-factor VIIa-specific up-regulation of IL-8 expression in MDA-MB-231 cells is mediated by PAR-2 and results in increased cell migration. Blood 2004; 103:3029-37.
(39) Albrektsen T, Sorensen B B, Hjorto G M, Fleckner J, Rao L V, Petersen L C. Transcriptional program induced by factor VIIa-tissue factor, PAR1 and PAR2 in MDA-MB-231 cells. J Thromb Haemost 2007; 5:1588-97.
(40) Bromberg M E, Konigsberg W H, Madison J F, Pawashe A, Garen A. Tissue factor promotes melanoma metastasis by a pathway independent of blood coagulation. Proc Natl Acad Sci USA 1995; 92:8205-9.
(41) Mueller B M, Ruf W. Requirement for binding of catalytically active factor VIIa in tissue factor-dependent experimental metastasis. J Clin Invest 1998; 101:1372-8.
(42) Tsuneyoshi N, Fukudome K, Horiguchi S, Ye X, Matsuzaki M, Toi M, et al. Expression and anticoagulant function of the endothelial cell protein C receptor (EPCR) in cancer cell lines. Thromb Haemost 2001; 85:356-61.
(43) Menschikowski M, Hagelgans A, Tiebel O, Klinsmann L, Eisenhofer G, Siegert G. Expression and shedding of endothelial protein C receptor in prostate cancer cells. Cancer Cell Int 2011; 11:4.
(44) Scheffer G L, Flens M J, Hageman S, Izquierdo M A, Shoemaker R H, Scheper R J. Expression of the vascular endothelial cell protein C receptor in epithelial tumour cells. Eur J Cancer 2002; 38:1535-42.
(45) Isermann B, Vinnikov I A, Madhusudhan T, Herzog S, Kashif M, Blautzik J, et al. Activated protein C protects against diabetic nephropathy by inhibiting endothelial and podocyte apoptosis. Nat Med 2007; 13:1349-58.
(46) Joyce D E, Gelbert L, Ciaccia A, Dehoff B, Grinnell B W. Gene expression profile of antithrombotic protein c defines new mechanisms modulating inflammation and apoptosis. J Biol Chem 2001; 276:11199-203.
(47) Cheng T, Liu D, Griffin J, Fernandez J, Castellino F, Rosen E, et al. Activated protein C blocks p53 mediated apoptosis in ischemic human brain endothelium and is neuroprotective. Nature Medicine 2003; 9:338-42.
(48) Guo H, Liu D, Gelbard H, Cheng T, Insalaco R, Fernandez J A, et al. Activated protein C prevents neuronal apoptosis via protease activated receptors 1 and 3. Neuron 2004; 41:563-72.
(49) Mosnier L O, Griffin J H Inhibition of staurosporine-induced apoptosis of endothelial cells by activated protein C requires protease-activated receptor-1 and endothelial cell protein C receptor. Biochem J 2003; 373:65-70.
(50) Mosnier L O, Zlokovic B V, Griffin J H. The cytoprotective protein C pathway. Blood 2007; 109:3161-72.
(51) Bae J S, Yang L, Manithody C, Rezaie A R. The ligand occupancy of EPCR switches the protease-activated receptor 1-dependent signaling specificity of thrombin from a permeability-enhancing to a barrier-protective response in endothelial cells. Blood 2007; 110:3909-16.
(52) Bae J S, Rezaie A R. Thrombin inhibits nuclear factor kappaB and RhoA pathways in cytokine-stimulated vascular endothelial cells when EPCR is occupied by protein C. Thromb Haemost 2009; 101:513-20.
(53) Joyce D E, Grinnell B W. Recombinant human activated protein C attenuates the inflammatory response in endothelium and monocytes by modulating nuclear factor-kappaB. Crit Care Med 2002; 30:5288-5293.
(54) Grivennikov S I, Greten F R, Karin M. Immunity, inflammation, and cancer. Cell 2010; 140:883-99.
(55) Yu H, Pardoll D, Jove R. STATs in cancer inflammation and immunity a leading role for STAT3. Nat Rev Cancer 2009; 9:798-809.
(56) Mantovani A, Allavena P, Sica A, Balkwill F. Cancer-related inflammation Nature 2008; 454:436-44.
(57) van der Most R G, Robinson B W, Nelson D J. Gene therapy for malignant mesothelioma: beyond the infant years. Cancer Gene Ther 2006; 13:897-904.
(58) Vachani A, Sterman D H, Albelda S M. Cytokine gene therapy for malignant pleural mesothelioma. J Thorac Oncol 2007; 2:265-7

The references cited above are all incorporated by reference herein, whether specifically incorporated or not. Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of sensitizing malignant pleural mesothelioma (MPM) cells to killing by endogenous cytokines in a subject in need thereof, said method comprising transducing MPM cells to express Endothelial Protein C Receptor (EPCR), by exposing them to a nucleic acid expression vector, wherein said vector is administered intrapleurally to said subject, the vector comprising a nucleotide sequence comprising:
   (i) an EPCR-coding sequence consisting of the nucleotide of SEQ ID NO:1 encoding the EPCR of SEQ ID NO:2, said nucleic acid EPCR-coding sequence operably linked to a promoter to express said EPCR-coding sequence in MPM cells, and said nucleic acid EPCR-coding sequence optionally linked to
   (ii) an enhancer and/or other expression control element for expression of EPCR in the MPM cells,
      wherein cells so transduced and expressing EPCR are sensitized to killing by endogenous cytokines interferon-γ (IFNγ) and tumor necrosis factor-α (TNFα) compared to MPM cells not so transduced that are not so sensitized to such killing.

2. A method of killing sensitized MPM cells which have been sensitized according to the method of claim 1, said method comprising exposing said transduced MPM cells to an effective amount of intrapleurally administered:
   (i) IFNγ which acts in combination with endogenous TNFα in such killing, or
   (ii) combination of IFNγ and TNFα which together kill said sensitized MPM cells.

3. The method of claim 1 wherein the promoter is:
   (a) CREBBP/EP300 inhibitory protein-1 gene promoter; or
   (b) mesothelin gene promoter further linked to a mesothelin gene enhancer element.

* * * * *

UNITED STATES PATENT AND TRADEMARK OFFICE
CERTIFICATE OF CORRECTION

PATENT NO. : 9,808,505 B2
APPLICATION NO. : 14/765922
DATED : November 7, 2017
INVENTOR(S) : Usha R. Pendurthi Page 1 of 1

It is certified that error appears in the above-identified patent and that said Letters Patent is hereby corrected as shown below:

In the Specification

Following the title of invention, at Column 1, add the following paragraph:
STATEMENT OF RIGHTS TO INVENTIONS MADE UNDER FEDERALLY SPONSORED RESEARCH
This invention was made with government support (NIH HL107183) awarded by the National Institutes at Health. The government has certain rights in the invention.

Signed and Sealed this
Nineteenth Day of March, 2019

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 717
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(717)

<400> SEQUENCE: 1 atg ttg aca aca ttg ctg ccg ata ctg ctg ctg tct ggc tgg gcc ttt      48
Met Leu Thr Thr Leu Leu Pro Ile Leu Leu Leu Ser Gly Trp Ala Phe
1               5                   10                  15 tgt agc caa gac gcc tca gat ggc ctc caa aga ctt cat atg ctc cag      96
Cys Ser Gln Asp Ala Ser Asp Gly Leu Gln Arg Leu His Met Leu Gln
            20                  25                  30
```

-continued

| | | |
|---|---|---|
| atc tcc tac ttc cgc gac ccc tat cac gtg tgg tac cag ggc aac gcg<br>Ile Ser Tyr Phe Arg Asp Pro Tyr His Val Trp Tyr Gln Gly Asn Ala<br>35                             40                       45 | | 144 |
| tcg ctg ggg gga cac cta acg cac gtg ctg gaa ggc cca gac acc aac<br>Ser Leu Gly Gly His Leu Thr His Val Leu Glu Gly Pro Asp Thr Asn<br>   50                         55                       60 | | 192 |
| acc acg atc att cag ctg cag ccc ttg cag gag ccc gag agc tgg gcg<br>Thr Thr Ile Ile Gln Leu Gln Pro Leu Gln Glu Pro Glu Ser Trp Ala<br>65                             70                       75                       80 | | 240 |
| cgc acg cag agt ggc ctg cag tcc tac ctc cag ttc cac ggc ctc<br>Arg Thr Gln Ser Gly Leu Gln Ser Tyr Leu Leu Gln Phe His Gly Leu<br>                      85                       90                       95 | | 288 |
| gtg cgc ctg gtg cac cag gag cgg acc ttg gcc ttt cct ctg acc atc<br>Val Arg Leu Val His Gln Glu Arg Thr Leu Ala Phe Pro Leu Thr Ile<br>                   100                      105                     110 | | 336 |
| cgc tgc ttc ctg ggc tgt gag ctg cct ccc gag ggc tct aga gcc cat<br>Arg Cys Phe Leu Gly Cys Glu Leu Pro Pro Glu Gly Ser Arg Ala His<br>             115                      120                     125 | | 384 |
| gtc ttc ttc gaa gtg gct gtg aat ggg agc tcc ttt gtg agt ttc cgg<br>Val Phe Phe Glu Val Ala Val Asn Gly Ser Ser Phe Val Ser Phe Arg<br>130                           135                      140 | | 432 |
| ccg gag aga gcc ttg tgg cag gca gac acc cag gtc acc tcc gga gtg<br>Pro Glu Arg Ala Leu Trp Gln Ala Asp Thr Gln Val Thr Ser Gly Val<br>145                         150                       155                  160 | | 480 |
| gtc acc ttc acc ctg cag cag ctc aat gcc tac aac cgc act cgg tat<br>Val Thr Phe Thr Leu Gln Gln Leu Asn Ala Tyr Asn Arg Thr Arg Tyr<br>                   165                      170                     175 | | 528 |
| gaa ctg cgg gaa ttc ctg gag gac acc tgt gtg cag tat gtg cag aaa<br>Glu Leu Arg Glu Phe Leu Glu Asp Thr Cys Val Gln Tyr Val Gln Lys<br>                180                      185                     190 | | 576 |
| cat att tcc gcg gaa aac acg aaa ggg agc caa aca agc cgc tcc tac<br>His Ile Ser Ala Glu Asn Thr Lys Gly Ser Gln Thr Ser Arg Ser Tyr<br>                   195                      200                     205 | | 624 |
| act tcg ctg gtc ctg ggc gtc ctg gtg ggc agt ttc atc att gct ggt<br>Thr Ser Leu Val Leu Gly Val Leu Val Gly Ser Phe Ile Ile Ala Gly<br>210                           215                      220 | | 672 |
| gtg gct gta ggc atc ttc ctg tgc aca ggt gga cgg cga tgt taa<br>Val Ala Val Gly Ile Phe Leu Cys Thr Gly Gly Arg Arg Cys<br>225                         230                      235 | | 717 |

<210> SEQ ID NO 2
<211> LENGTH: 238
<212> TYPE: PRT
<213> ORGANISM: Artificial Sequence
<220> FEATURE:
<223> OTHER INFORMATION: Synthetic Construct

<400> SEQUENCE: 2

Met Leu Thr Thr Leu Leu Pro Ile Leu Leu Leu Ser Gly Trp Ala Phe
1               5                   10                  15

Cys Ser Gln Asp Ala Ser Asp Gly Leu Gln Arg Leu His Met Leu Gln
                20                  25                  30

Ile Ser Tyr Phe Arg Asp Pro Tyr His Val Trp Tyr Gln Gly Asn Ala
            35                  40                  45

Ser Leu Gly Gly His Leu Thr His Val Leu Glu Gly Pro Asp Thr Asn
        50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
            100                 105                 110

Arg Cys Phe Leu Gly Cys Glu Leu Pro Pro Glu Gly Ser Arg Ala His
        115                 120                 125

Val Phe Glu Val Ala Val Asn Gly Ser Ser Phe Val Ser Phe Arg
    130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
        195                 200                 205

Thr Ser Leu Val Leu Gly Val Leu Val Gly Ser Phe Ile Ile Ala Gly
    210                 215                 220

Val Ala Val Gly Ile Phe Leu Cys Thr Gly Gly Arg Arg Cys
225                 230                 235

<210> SEQ ID NO 3
<211> LENGTH: 556
<212> TYPE: DNA
<213> ORGANISM: Artificial Sequence
<220> FEATURE:
<223> OTHER INFORMATION: Synthetic

<400> SEQUENCE: 3
cctcccccag gcctggcccg ctgcctgtcc aaggctcctg tgcggggtct ccacccacac      60
attcctgggg cgtgaggcgc caccactccc tgctccccgg gcaaagccgc tcatttgttc     120
cctttgacgg cccggaggc tgccaggctc tcaccccca cttcccaatt gaggaaaccg      180
aggcagagga ggctcaggtg tggccaatca ccctgcacat cagagttacc ctgggcaggg     240
cccactgaga cctgggaggg gccactcggg acctggaggg ctggggctg cccgggcgtt      300 aggggtaaag ctccctaccc aactgcgcag aaggcctcag aggcctgggg gctgggcttc    360 cccttttcaca tcgcccttta gaggcccacg tgtgggcatt ggcccgcgat ctgaaagggg    420
ctgtcctgtt cctcatgggc gctgccagcg ccacgcactc ctctttctgc ctggccggcc   480
actcccgtct gctgtgacgc gcggacagag agctaccggt ggacccacgg tgcctccctc    540
cctccctggg atctgt                                                     556

<210> SEQ ID NO 4
<211> LENGTH: 87
<212> TYPE: DNA
<213> ORGANISM: Artificial Sequence
<220> FEATURE:
<223> OTHER INFORMATION: Synthetic

<400> SEQUENCE: 4
atttgttccc tttgacggcc cgggaggctg ccaggctctc acccccccac ttcccaattg     60
aggaaaccga ggcagaggag gctcagg                                         87

<210> SEQ ID NO 5
<211> LENGTH: 19
<212> TYPE: DNA
<213> ORGANISM: Artificial Sequence
<220> FEATURE:
<223> OTHER INFORMATION: Synthetic

```
<400> SEQUENCE: 5
gaagcagacg tacttggca                                            19

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gcgcttcagg cactacaaat                                           20

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
aggctctact atgcctacta ct                                        22
```